US011904015B2

(12) United States Patent
Bedu-Addo et al.

(10) Patent No.: US 11,904,015 B2
(45) Date of Patent: *Feb. 20, 2024

(54) VACCINE COMPOSITIONS AND METHODS OF USE

(71) Applicant: PDS BIOTECHNOLOGY CORPORATION, North Brunswick, NJ (US)

(72) Inventors: Frank Bedu-Addo, Bethel, CT (US); Eric Jacobson, Cincinnati, OH (US); Kenya Johnson, Mason, OH (US)

(73) Assignee: PDS BIOTECHNOLOGY CORPORATION, Berkeley Heights, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/388,291

(22) Filed: Apr. 18, 2019

(65) Prior Publication Data

US 2019/0358318 A1 Nov. 28, 2019

Related U.S. Application Data

(63) Continuation of application No. 14/429,123, filed as application No. PCT/US2013/061132 on Sep. 23, 2013, now abandoned.

(60) Provisional application No. 61/703,814, filed on Sep. 21, 2012.

(51) Int. Cl.
*A61K 39/39* (2006.01)
*A61K 39/12* (2006.01)
*A61K 39/02* (2006.01)
*A61K 39/145* (2006.01)
*A61K 39/00* (2006.01)

(52) U.S. Cl.
CPC .......... *A61K 39/39* (2013.01); *A61K 39/0002* (2013.01); *A61K 39/0005* (2013.01); *A61K 39/02* (2013.01); *A61K 39/12* (2013.01); *A61K 39/145* (2013.01); *A61K 2039/55511* (2013.01); *A61K 2039/55555* (2013.01); *A61K 2039/70* (2013.01); *C12N 2760/16034* (2013.01); *C12N 2760/16134* (2013.01); *C12N 2760/16234* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2,167,480 | A | 7/1939 | Hansell |
| 4,703,004 | A | 10/1987 | Hopp et al. |
| 5,264,618 | A | 11/1993 | Felgner et al. |
| 5,283,185 | A | 2/1994 | Epand et al. |
| 5,334,761 | A | 8/1994 | Gebeyehu et al. |
| 5,459,127 | A | 10/1995 | Felgner et al. |
| 5,827,703 | A | 10/1998 | Debs et al. |
| 6,008,202 | A | 12/1999 | Huang et al. |
| 6,124,270 | A | 9/2000 | Haensler |
| 6,183,745 | B1 | 2/2001 | Tindle et al. |
| 6,214,804 | B1 | 4/2001 | Felgner et al. |
| 6,419,931 | B1 | 7/2002 | Vitiello et al. |
| 6,464,980 | B1 | 10/2002 | Fikes et al. |
| 6,586,409 | B1 | 7/2003 | Wheeler |
| 6,610,321 | B2 | 8/2003 | Huang et al. |
| 6,649,170 | B1 | 11/2003 | Lindblad et al. |
| 6,693,086 | B1 | 2/2004 | Dow et al. |
| 6,710,035 | B2 | 3/2004 | Felgner et al. |
| 6,780,421 | B1 | 8/2004 | Haensler et al. |
| 6,852,334 | B1 | 2/2005 | Cullis et al. |
| 7,001,614 | B2 | 2/2006 | Smyth-Templeton et al. |
| 7,105,574 | B1 | 9/2006 | Wheeler |
| 7,303,881 | B2 | 12/2007 | Huang et al. |
| 7,488,791 | B2 | 2/2009 | Maillere et al. |
| 8,877,206 | B2 | 11/2014 | Chen et al. |
| 9,102,950 | B2 | 8/2015 | Hartikka et al. |
| 9,789,129 | B2 | 10/2017 | Vasievich et al. |
| 10,155,049 | B2 | 12/2018 | Bonnet et al. |
| 10,286,064 | B2 | 5/2019 | Johnson et al. |
| 10,702,541 | B2 | 7/2020 | Vasievich et al. |
| 10,828,364 | B2 | 11/2020 | Johnson et al. |
| 11,401,306 | B2 | 8/2022 | Bedu-Addo et al. |
| 2001/0026937 | A1 | 10/2001 | Punnonen et al. |

(Continued)

FOREIGN PATENT DOCUMENTS

CN 1909918 A 2/2007
CN 101065350 A 10/2007

(Continued)

OTHER PUBLICATIONS

European Office Action from corresponding European Application No. 13 839 199.0; dated Nov. 13, 2017.

(Continued)

*Primary Examiner* — Benjamin P Blumel
(74) *Attorney, Agent, or Firm* — DLA Piper LLP (US)

(57) ABSTRACT

The present disclosure provides vaccine compositions comprising at least one adjuvant and at least one antigen, wherein the adjuvant is a cationic lipid. The disclosure also provides methods of treating a disease in a mammal, methods of preventing a disease in a mammal, and methods of effecting antigen cross presentation to induce a humoral immune response and a cellular immune response in a mammal utilizing the vaccine compositions. Cross presentation of various antigens can be achieved by formulating the specific antigens with cationic lipids possessing adjuvant properties.

18 Claims, 5 Drawing Sheets

Specification includes a Sequence Listing.

(56) References Cited

U.S. PATENT DOCUMENTS

| | | |
|---|---|---|
| 2002/0007173 A1* | 1/2002 | Kundig .............. A61K 39/00 604/522 |
| 2002/0187105 A1 | 12/2002 | Zou et al. |
| 2003/0008813 A1 | 1/2003 | Felgner et al. |
| 2003/0229040 A1 | 12/2003 | Kasid et al. |
| 2004/0106551 A1 | 6/2004 | Khleif et al. |
| 2004/0157791 A1 | 8/2004 | Dow et al. |
| 2004/0185057 A1 | 9/2004 | Kirkby et al. |
| 2004/0203051 A1 | 10/2004 | Simard et al. |
| 2005/0025822 A1 | 2/2005 | Wong et al. |
| 2005/0112559 A1 | 5/2005 | Leung et al. |
| 2005/0176672 A1 | 8/2005 | Scheule et al. |
| 2005/0220814 A1 | 10/2005 | Dominowski et al. |
| 2005/0245446 A1 | 11/2005 | Hailes et al. |
| 2006/0008472 A1 | 1/2006 | Huang et al. |
| 2006/0051405 A1 | 3/2006 | MacLachlan et al. |
| 2006/0083780 A1 | 4/2006 | Heyes et al. |
| 2006/0159738 A1 | 7/2006 | Graham et al. |
| 2006/0165708 A1 | 7/2006 | Mayumi et al. |
| 2006/0171956 A1 | 8/2006 | Bareholz et al. |
| 2006/0182793 A1 | 8/2006 | Bachmann et al. |
| 2006/0204566 A1 | 9/2006 | Smyth-Templeton et al. |
| 2006/0223769 A1 | 10/2006 | Dow et al. |
| 2006/0251726 A1 | 11/2006 | Lin et al. |
| 2006/0263804 A1 | 11/2006 | Robinson et al. |
| 2006/0275777 A1 | 12/2006 | Waelti |
| 2006/0286124 A1 | 12/2006 | Burt et al. |
| 2007/0014807 A1 | 1/2007 | Maida, III |
| 2007/0059318 A1 | 3/2007 | Balu-Iyer et al. |
| 2007/0066552 A1 | 3/2007 | Clarke et al. |
| 2007/0207526 A1 | 9/2007 | Coit et al. |
| 2008/0014251 A1 | 1/2008 | Benz et al. |
| 2008/0014254 A1 | 1/2008 | Platscher et al. |
| 2008/0049957 A1 | 2/2008 | Topholm |
| 2008/0131455 A1 | 6/2008 | Huang et al. |
| 2008/0152665 A1 | 6/2008 | Leclerc et al. |
| 2008/0206286 A1 | 8/2008 | Yu |
| 2008/0248044 A1 | 10/2008 | Choppin et al. |
| 2009/0001705 A1 | 1/2009 | Fischer et al. |
| 2009/0017057 A1 | 1/2009 | Chen et al. |
| 2009/0053251 A1 | 2/2009 | Pogue-Caley et al. |
| 2010/0086584 A1 | 4/2010 | Callejo et al. |
| 2010/0099745 A1* | 4/2010 | Sambhara ............ A61K 39/145 514/44 R |
| 2010/0112002 A1 | 5/2010 | Lien et al. |
| 2010/0158939 A1 | 6/2010 | Sambhara et al. |
| 2010/0203080 A1 | 8/2010 | Maillere et al. |
| 2010/0221223 A1 | 9/2010 | Tsutsui et al. |
| 2010/0239657 A1 | 9/2010 | Kim et al. |
| 2010/0266547 A1 | 10/2010 | Benedict |
| 2010/0297144 A1 | 11/2010 | Roden |
| 2011/0110972 A1 | 5/2011 | Vasievich et al. |
| 2011/0117141 A1 | 5/2011 | Huang et al. |
| 2011/0158952 A1 | 6/2011 | Beach et al. |
| 2011/0305713 A1 | 12/2011 | Munn et al. |
| 2012/0148622 A1 | 6/2012 | Tenoever |
| 2013/0129761 A1 | 5/2013 | Garcia-Sastre et al. |
| 2013/0225663 A1 | 8/2013 | Brown |
| 2013/0243723 A1 | 9/2013 | Hadden et al. |
| 2015/0079155 A1 | 3/2015 | Jensen et al. |
| 2015/0093410 A1 | 4/2015 | Chen et al. |
| 2015/0110823 A1 | 4/2015 | Bedu-Addo et al. |
| 2015/0132340 A1 | 5/2015 | Johnson et al. |
| 2015/0250872 A1 | 9/2015 | Bedu-Addo et al. |
| 2015/0283219 A1 | 10/2015 | Langlade Demoyen et al. |
| 2015/0343062 A1 | 12/2015 | Kuboyama et al. |
| 2016/0168227 A1 | 6/2016 | Kallen et al. |
| 2016/0193316 A1 | 7/2016 | Sette et al. |
| 2016/0251406 A1 | 9/2016 | Schlom et al. |
| 2017/0296639 A1 | 10/2017 | Ma et al. |
| 2018/0015114 A1 | 1/2018 | Vasievich et al. |
| 2018/0094032 A1 | 4/2018 | Bedu-Addo et al. |
| 2018/0221475 A1 | 8/2018 | Bedu-Addo et al. |
| 2018/0353599 A1 | 12/2018 | Bedu-Addo et al. |
| 2019/0321321 A1 | 10/2019 | Bedu-Addo et al. |
| 2019/0358319 A1 | 11/2019 | Bedu-Addo et al. |

FOREIGN PATENT DOCUMENTS

| | | |
|---|---|---|
| CN | 101193655 A | 6/2008 |
| CN | 101702882 A | 5/2010 |
| CN | 102137675 A | 7/2011 |
| CN | 104189897 A | 12/2014 |
| CN | 104703588 A | 6/2015 |
| CN | 105163753 A | 12/2015 |
| CN | 105920599 A | 9/2016 |
| CN | 111217918 A | 6/2020 |
| EP | 2167480 A2 | 3/2010 |
| JP | H06510051 A | 11/1994 |
| JP | H09502086 A | 3/1997 |
| JP | H10501822 A | 2/1998 |
| JP | 2002537102 A | 11/2002 |
| JP | 2002542341 A | 12/2002 |
| JP | 2003506095 A | 2/2003 |
| JP | 2003509035 A | 3/2003 |
| JP | 2004508012 A | 3/2004 |
| JP | 2006513979 A | 4/2006 |
| JP | 2006527762 A | 12/2006 |
| JP | 2007238559 A | 9/2007 |
| JP | 2008521757 A | 6/2008 |
| JP | 2010522206 A | 7/2010 |
| JP | 2010537961 A | 12/2010 |
| JP | 2011518170 A | 6/2011 |
| JP | 2012526853 A | 11/2012 |
| JP | 2014527965 A | 10/2014 |
| RU | 2311911 C2 | 12/2007 |
| TW | I589298 B | 7/2017 |
| WO | WO-9303709 A1 | 3/1993 |
| WO | WO-9303764 A1 | 3/1993 |
| WO | WO-9322338 A1 | 11/1993 |
| WO | WO-9504542 A1 | 2/1995 |
| WO | WO-9527508 A1 | 10/1995 |
| WO | WO-9703703 A1 | 2/1997 |
| WO | WO-0050006 A2 | 8/2000 |
| WO | WO-0062813 A2 | 10/2000 |
| WO | WO-0077043 A2 | 12/2000 |
| WO | WO-0111067 A1 | 2/2001 |
| WO | WO-0119408 A1 | 3/2001 |
| WO | WO-0180900 A2 | 11/2001 |
| WO | WO-02069369 A2 | 9/2002 |
| WO | WO-02097116 A2 | 12/2002 |
| WO | WO-03011252 A1 | 2/2003 |
| WO | WO-03095641 A1 | 11/2003 |
| WO | WO-2004014957 A1 | 2/2004 |
| WO | WO 2004089413 A1 | 10/2004 |
| WO | WO 2005000889 A1 | 1/2005 |
| WO | WO-2006063382 A1 | 6/2006 |
| WO | WO-2007022152 A2 | 2/2007 |
| WO | WO-2007121895 A2 | 11/2007 |
| WO | WO-2008116078 A2 | 9/2008 |
| WO | WO-2008148057 A2 | 12/2008 |
| WO | WO-2008116078 A4 | 10/2009 |
| WO | WO-2009129227 A1 | 10/2009 |
| WO | WO-2009142892 A1 | 11/2009 |
| WO | WO-2010101663 A2 | 9/2010 |
| WO | WO-2013016675 A1 | 1/2013 |
| WO | WO-2013188627 A2 | 12/2013 |
| WO | WO-2014047533 A1 | 3/2014 |
| WO | WO-2015061416 A2 | 4/2015 |
| WO | WO-2015176662 A1 | 11/2015 |
| WO | WO-2016146618 A1 | 9/2016 |
| WO | WO-2017083820 A1 | 5/2017 |

OTHER PUBLICATIONS

Third Chinese Office Action, along with its translation, from corresponding Chinese Application No. 201380060902.8; dated Oct. 18, 2017.

Second Office Action and Supplementary Search Report for corresponding Chinese Application No. 201380060902.8; dated Mar. 31, 2017.

(56) References Cited

OTHER PUBLICATIONS

Examination Report No. 1 for corresponding Australian Application No. 2013317805; dated Jul. 11, 2017.
Office Action dated Apr. 24, 2017, from corresponding Taiwan Application No. 102134251, along with an English translation.
Walker et al., "Cationic lipids direct a viral glycoprotein into the class I major histocompatibility complex antigen-presentation pathway", PNAS, 1992, vol. 89, pp. 7915-7918.
Joseph et al., "A new intranasal influenza vaccine based on a novel polycationic lipid-ceramide carbamoyl-spermine (CCS) I. Immunogenicity and efficacy studies in mice", 2006, Vaccine, vol. 24, pp. 3990-4006.
GenBank Accession # AFO65027, hemagglutinin [Influenza A virus (A/New Caldeonia/20/1999(H1N1))], Jul. 26, 2012.
Chen et al., "A simple but effective cancer vaccine consisting of an antigen and a cationic lipid", 2008, Cancer Immunology, Immunotherapy, vol. 57, pp. 517-520.
Chinese First Office Action dated May 26, 2016, of corresponding Chinese Application No. 201380060902.8, along with an English translation.
Hartikka et al., Vaxfectin®, a cationic lipid-based adjuvant for protein-based influenza vaccines, 2009, Vaccine, vol. 27, pp. 6399-6403.
Weiss, Amélie et al., "Intracellular peptide delivery using amphiphilic lipid-based formulations," Biotechnology and Bioengineering., vol. 108, No. 10, Apr. 25, 2011, pp. 2477,2487.
Supplementary European Search Report dated Apr. 4, 2016, from corresponding European Application No. 13839199.0.
Bei et al., "The use of a cationic liposome (DOTAP) mixed with a recombinant tumor-associated antigen to induce responses and protective immunity in mice", J Immunother., 21(2), pp. 159-169, 1998.
Walker, Christopher et al., "Cationic lipids direct a viral glycoprotein into the class 1 major histocompatibility complex antigen-presentation pathway", Proc. Natl. Acad. Sci. USA, 1992, vol. 89, pp. 7915-7918.
Second Examiner's Report and Examination Search Report from counterpart Canadian Patent Appln. No. 2885741 dated Aug. 10, 2020.
Third Examiner's Report and Examination Search Report from counterpart Canadian Patent Appln. No. 2885741 dated Jun. 30, 2021, along with a Request to Withdraw Report dated Aug. 25, 2021.
"3,5,9-Trioxa-4-phosphaheptacos-18-en-1-aminium, 4-ethoxy-N, N, N-trimethyl-10-oxo-7-[[(9Z)-1-oxo-9-octadecen-1-yl]oxy]-, 4-oxide, (7R,18Z)-," Registry, Chemical Abstracts Service, Columbus, Ohio, US, Database Accession No. 183283-20-7, Nov. 22, 1996, 02 pages, XP002694550.
Alving C.R., "Design And Selection Of Vaccine Adjuvants: Animal Models And Human Trials," Vaccine, Elsevier Science Ltd, 2002, vol. 20, pp. S56-S64.
Anderson P., "Effective Vaccination of Mice Against *Mycobacterium tuberculosis* Infection With A Soluble Mixture of Secreted Mycobacterial Proteins," Infection and Immunity, American Society for Microbiology, Jun. 1994, vol. 62, No. 6, pp. 2536-2544.
Aramaki Y., et al., "Induction of Apoptosis in WEHI 231 Cells by Cationic Liposomes," Pharmaceutical Research, Plenum Publishing Corporation, Jan. 18, 2000, vol. 17, No. 5, pp. 515-520.
Baecher-Allan C., et al., "Immune Regulation In Tumor-Bearing Hosts," Current Opinion In Immunology, Elsevier Limited, 2006, vol. 18, pp. 214-219.
Baecher-Allan C., et al., "Suppressor T Cells in Human Diseases," Journal of Experimental Medicine, The Rockefeller University Press, Aug. 2, 2004, vol. 200, No. 3, pp. 273-276.
Banchereau J., et al., "Dendritic Cells And The Control of Immunity," Nature, Mar. 19, 1998, vol. 392, No. 6673, pp. 245-252.
Bei R., et al., "The Use of a Cationic Liposome Formulation (DOTAP) Mixed with a Recombinant Tumor-Associated Antigen to Induce Immune Responses and Protective Immunity in Mice," Journal of Immunotherapy, 1998, vol. 21, No. 3, 2 Pages, Abstract only.
Benmohamed L., et al., Lipopetide Immunization Without Adjuvant Induces Potent And Long-Lasting B, T Helper, And Cytotoxic T Lymphocyte Resonses Against A Malaria Liver Stage Antigen In Mice And Chimpanzees, European Journal Of Immunology, VCH Verlagsgesellschaft, 1997, vol. 27, pp. 1242-1253.
Berraondo P., et al., "Eradication of Large Tumors in Mice by a Tritherapy Targeting the Innate, Adaptive, and Regulatory Components of the Immune System," Cancer Research, American Association for Cancer Research, US, Sep. 15, 2007, vol. 67, No. 18, pp. 8847-8855, DOI:10.1158/0008-5472.CAN-07-0321, ISSN 0008-5472, XP002673813.
Black M., et al., "Advances In The Design And Delivery Of Peptide Subunit Vaccines With A Focus On Toll-like Receptor Agonists." Expert Rev. Vaccines, vol. 9, No. 2, 2010, pp. 157-173.
Brunel F., et al., "Cationic Lipid DC-Chol Induces an Improved and Balanced Immunity Able to Overcome the Unresponsiveness to the Hepatitis B Vaccine," Vaccine, Apr. 1999, vol. 17, pp. 2192-2203.
Brunette E., et al., "Lipofection Does Not Require the Removal of Serum," Nucleic Acids Research, Cancer Research Institute, University Of California San Francisco Medical Center, San Francisco, California, Dec. 26, 1991, vol. 20, No. 5, p. 1151.
Byers A.M., et al., "Cutting Edge: Rapid In Vivo CTL Activity by Polyoma Virus-Specific Effector and Memory CD8+ T Cells," The American Association of Immunologists Inc., The Journal of Immunology, 2003, vol. 171, pp. 17-21.
Cantor H., et al., "Immunoregulatory Circuits Among T-Cell Sets II. Physiologic Role of Feedback Inhibition in Vivo: Absence in NZB Mice," The Rockefeller University Press, Journal of Experimental Medicine, 1978, pp. 1116-1125.
Carr M.W., et al., "Monocyte Chemoattractant Protein 1 Acts As AT-Lymphocyte Chemoattractant," Proceedings Of The National Academy Of Sciences of The United States Of America, Committee On Immunology and Department Of Pathology, Harvard Medical School, Department Of Cardiology, Childen's Hospital, and The Center For Blood Research, Boston, Massachusetts, Apr. 1994, vol. 91, pp. 3652-3656.
Castellino F., et al., "Chemokine-Guided CD4+ T Cell Help Enhances Generation Of IL-6Ra high IL-7Ra high Prememory COB+ T Cells," The Journal Of Immunology, Lymphocyte Biology Section, Laboratory Of Immunology, National Institute Of Allergy And Infectious Diseases, National Institutes Of Health, Bethesda, Maryland, 2007, vol. 178, pp. 778-787.
Castellino F., et al., "Chemokines Enhance Immunity By Guiding Naive COB+ T Cells To Sites Of CD4+ T Cell-Dendritic Cell Interaction," Nature, Lymphocyte Biology Section, Laboratory Of Immunology, National Institute Of Allergy And Infectious Diseases, National Institutes Of Health, Bethesda, Maryland, Apr. 13, 2006, vol. 440, pp. 890-895.
Chen W., et al., "A Simple and Effective Cancer Vaccine Consisting of an Antigen and a Cationic Lipid," Division of Molecular Pharmaceutics, School of Pharmacy, University of North Carolina, Chapel Hill, Chapel Hill, North Carolina, USA, 2008, pp. 1-48.
Chen W., et al., "Induction of Cytotoxic T-Lymphocytes and Antitumor Activity by a Liposomal Lipopeptide Vaccine," Molecular Pharmaceutics, 2008, vol. 5, No. 3, pp. 464-471.
Chen W.C., et al., "Cationic Liposome-Based Peptide Vaccine: Potent Therapeutics for Cervical Cancer," Poster, School of Pharmacy, May 20, 2006, 1 Page.
Chikh G., et al., "Liposomal Delivery of CTL Epitopes to Dendritic Cells, Bioscience Reports," Plenum Publishing Corporation, Apr. 2002, vol. 22, No. 2, pp. 339-353.
Christensen D., et al., "Cationic Liposomes as Vaccine Adjuvants," Expert Review of Vaccines, Oct. 2007, vol. 6, No. 5, pp. 785-796, XP008137314.
Cohen P. A., et al., "CD4+ T-Cells From Mice Immunized To Syngeneic Sarcomas Recognize Distinct, Non-Shared Tumor Antigens," Cancer Research, Branches Of Surgery And Dermatology, National Cancer Institute, National Institute Of Health, Bethesda, Maryland, Feb. 15, 1994, vol. 54, pp. 1055-1058.

(56) References Cited

OTHER PUBLICATIONS

Comes A., et al., "CD25+ Regulatory T Cell Depletion Augments Immunotherapy of MicroMetastases by an IL-21-Secreting Cellular Vaccine1," The Journal of Immunology, The American Association of Immunologists Incorporated, 2006, pp. 1750-1758.
Communication about Intention to Grant a European Patent received for European Application No. 08799629.4, dated Jun. 1, 2015, 6 Pages.
Communication about Intention to Grant a European Patent Received for European Application No. 09733034.4, dated Jul. 6, 2018, 6 Pages.
Communication about Intention to Grant a European Patent Received for European Application No. 12831495.2, dated Feb. 16, 2018, 10 Pages.
Communication about Intention to Grant a European Patent Received for European Application No. 13804165.2, dated May 9, 2019, 7 Pages.
Connor J., et al., "pH-Sensitive Immunoliposomes as an Efficient and Target-Specific Carrier for Antitumor Drugs," Cancer Research, Department of Biochemistry, University of Tennessee, KnoxvilleTennessee, Jul. 1986, vol. 46, pp. 3431-3435.
Copland M.J., et al., "Lipid Based Particulate Formulations for the Delivery of Antigen," Immunology and Cell Biology, Australasian Society for Immunology Incorporate, 2005, vol. 83, pp. 97-105.
Credo Reference, 2005.
Cui Z., et al., "Coating of Mannan on LPD Particles Containing HPV E7 Peptide Significantly Enhances Immunity Against HPV-Positive Tumor," Pharmaceutical Research, Jun. 2004, vol. 21, No. 6, pp. 1018-1025.
Cui Z., et al., "Immunostimulation Mechanism of LPD Nanoparticle as a Vaccine Carrier," Molecular Pharmaceutics, American Chemical Society, 2005, vol. 2, No. 1, pp. 22-28.
Cui Z., et al., "Liposome-Polycation-DNA (LPD) Particle As A Carrier and Adjuvant for Protein-Based Vaccines: Therapeutic Effect Against Cervical Cancer," Cancer Immunology and Immunother, Springer-Verlag, 2005, vol. 54, pp. 1180-1190.
Datta G., et al., "Effects of Increasing Hydrophobicity on the Physical-Chemical and Biological Properties of a Class A Amphipathic Helical Peptide," Journal of Lioid Research, 2001, vol. 42, pp. 1096-1104.
Davies G., "Adjuvant Activity of Cytokines," Chapter 19, Methods in Molecular Biology, 2010, ISSN: 0003658713, pp. 287-309.
De Bruijn M.L.H., et al., "Immunization With Human Papillomavirus Type 16 (Hpv16) Oncoproteinoloaded Dendritic Cells As Well As Proteinin Adjuvant Induces Mhc Class 1-restricted Protection To Hpv16-induced Tumor Cells," Cancer Research, Feb. 15, 1998, vol. 58, No. 4, pp. 724-731.
Decision of Rejection from Corresponding Japanese Patent Application No. JP2018524752, dated Jul. 13, 2021, 6 Pages.
Decision on the Request for Reexamination from Corresponding Chinese Application No. 200880017151.0, dated Jun. 12, 2017, 18 pages.
Decision to Grant a European Patent received for European Application No. 08799629.4, dated Oct. 15, 2015, 3 Pages.
Decision to Grant a European Patent received for European Application No. 09733034.4, dated Oct. 25, 2018, 2 Pages.
Decision to Grant a European Patent Received for European Application No. 12831495.2, dated Jun. 7, 2018, 2 Pages.
Decision to Grant a European Patent received for European Application No. 13804165.2, dated Sep. 19, 2019, 3 Pages.
Decker T., et al., "The Yin and Yang of Type I Interferon Activity in Bacterial Infection," Nature Reviews Immunology, 2005, vol. 5, pp. 675-687.
Denning D.W., et al., "Micafungin (FK463), Alone or in Combination with Other Systemic Antifungal Agents, for the Treatment of Acute Invasive Aspergillosis," Journal Of Infection, Elsevier Ltd, 2006, vol. 53, pp. 337-349.
DeSilva D.R, et al., "The p38 Mitogen-Activated Protein Kinase Pathway in Activated and Anergic Th1 Cells," Cellular Immunology, Academic Press, 1997, vol. 180, pp. 116-123.

Diamond D.J., et al., "Development of a Candidate HLA A*0201 Restricted Peptide-Based Vaccine Against Human Cytomegalovirus Infection," Blood, Sep. 1, 1997, vol. 90, No. 05, pp. 1751-1767.
Dileo J., et al., "Lipid-Protamine-DNA-Mediated Antigen Delivery to Antigen-Presenting Cells Results in Enhanced Anti-Tumor Immune Responses," The American Society of Gene Therapy, Molecular Therapy, May 2003, vol. 7, No. 5, pp. 640-648.
Dillon S., et al., "A Toll-Like Receptor 2 Ligand Stimulates Th2 Responses In Vivo, Via Induction Of Extracellular Signal-Regulated Kinase Mitogen-Activated Protein Kinase and c-Fos In Dendritic Cells," The Journal Of Immunology, The American Association Of Immunologists, Inc., 2004, vol. 172, 12 Pages.
Dolcetti L., et al., "Hierarchy of Immunosuppressive Strength Among Myeloid-derived Suppressor Cell Subsets is determined by GM-CSF," European Journal of Immunology, 2010, vol. 40, pp. 22-35.
Dong C., et al., "MAP Kinases in the Immune Response," Annual Review of Immunology, Annual Reviews, 2002, vol. 20, pp. 55-72.
Dow S.W., et al., "Lipid-DNA Complexes Induce Potent Activation of Innate Immune Responses and Antitumor Activity When Administered Intravenously," The Journal of Immunology, 1999, vol. 163, pp. 1552-1561.
Dranoff G., "GM-CSF-Based Cancer vaccines," Immunological Reviews, 2002, vol. 188, pp. 147-154.
Dupuis M., et al., "Dendritic Cells Internalize Vaccine Adjuvant After Intramuscular Injection," Cellular Immunology, Academic Press, 1998, vol. 186, pp. 18-27.
Eardley D.D., et al., "Immunoregulatory Circuits Among T-Cell Sets I. T-Helper Cells Induce Other T-Cell Sets to Exert Feedback Inhibition," The Rockefeller University Press, Journal of Experimental Medicine, 1978, pp. 1106-1115.
EMBL Database Entry GG774706, *bacteroides* sp. 1_ 1_ 14 Genomic Scaffold Supercont1.5, Jun. 15, 2010, 202 Pages, [Retrieved on Oct. 28, 2013), Retrieved from the Internet: http://www.ebi.ac.uk/ena/data/view/GG774706&display=text.
English Translation of First Office Action from Corresponding Chinese Application No. 201710819740.1, dated Jul. 17, 2020, 21 Pages.
English Translation of First Office Action in Counterpart Chinese Application No. 201880088575.X, dated Dec. 29, 2021, 21 Pages.
English Translation of Fist Office Action from Corresponding Chinese Patent Application No. 201710819740.1, dated Apr. 29, 2021, 15 Pages.
English Translation of Notice of Reasons for Refusal Received in Corresponding Japanese Patent Application No. 2018-524752 dated Sep. 3, 2020, 8 Pages.
English Translation of Notification of Defects from Corresponding Israel Application No. 259294, dated May 5, 2021, 6 Pages.
English translation of Notification of Reasons for Rejection from Corresponding Japanese Application No. 2014-17712, dated Sep. 15, 2015, 11 Pages.
English Translation of Office Action in Taiwanese Application No. 101133392, dated Nov. 2, 2015, 16 pages.
English Translation of Office Action Japanese Application No. JP2014529976, dated Jul. 11, 2017, 07 pages.
English Translation of Taiwanese Office Action for Corresponding Taiwanese Application No. 102121266, dated Jun. 20, 2016, 8 Pages.
English Translation of Third Office Action from Corresponding Chinese Application No. 200980121761.X, dated May 9, 2016, 10 Pages.
European Communication Corresponding European Application No. EP12831495.2 dated Jun. 6, 2016, 5 pages.
European Search Report and Written Opinion prepared for EP12831495 completed on Mar. 5, 2015, 8 Pages.
Examination Report No. 2 from Corresponding Australian Patent Application No. 2017340407, dated Jan. 6, 2021, 5 Pages.
Extended European Search Report for European Application No. 13804165.2, dated Jan. 5, 2016, 5 Pages.
Extended European Search Report for European Application No. 16865201.4, dated Jun. 6, 2019, 10 Pages.
Extended European Search Report for European Application No. 17859111.1, dated May 26, 2020, 7 Pages.

(56) References Cited

OTHER PUBLICATIONS

Extended European Search Report for European Application No. 18886648.7, dated Aug. 11, 2021, 9 Pages.
Extended European Search Report for European Application No. 19203293.6, dated Mar. 10, 2020, 6 Pages.
Extended European Search Report for European Application No. 08799629.4, dated Mar. 5, 2010, 04 Pages.
Extended European Search Report for European Application No. 09733034.4, dated Apr. 15, 2013, 07 Pages.
Extended European Search Report for European Application No. 12831495.2, dated Mar. 16, 2015, 09 Pages.
Felnerova D., et al., "Liposomes and Virosomes as Delivery Systems for Antigens," Nucleic Acids and Drugs, Current Opinion in Biotechnology, Elsevier Ltd, 2004, vol. 15, pp. 518-529.
Feltkamp M.C., et al., "Vaccination with Cytotoxic T Lymphocyte Epitope-containing Peptide Protects Against a Tumor Induced by Human Papillomavirus Type 16-transformed Cells," European Journal Of Immunology, PubMed, Sep. 1993, vol. 23, No. 9, pp. 2242-2249.
Fernandes I., et al., "Synthetic Lipopeptides Incorporated In Liposomes: In Vitro Stimulation Of The Profliferation Of Murine Splenocytes And In Vivo Induction Of An Immune Response Against A Peptide Antigen," Molecular Immunology, Elsevier Limited, 1997, vol. 34, No. 8/9, pp. 569-576.
Filion M.C., et al., "Anti-Inflammatory Activity of Cationic Lipids," British Journal Of Pharmacology, Oct. 1997, vol. 122, No. 3, pp. 551-557, ISSN 0007-1188, XP002569679.
Filion M.C., "Major Limitations in the Use of Cationic Liposomes for DNA Delivery," International Journal of Pharmaceutics, 1998, vol. 162, No. 1-2, pp. 159-170.
Final Office Action from Corresponding U.S. Appl. No. 15/775,680, dated Jan. 22, 2021, 9 Pages.
First Examination Report from Corresponding Indian Patent Application No. 201618020440, dated Nov. 10, 2020, 4 Pages.
First Examination Report from counterpart Indian Application No. 11144/DELNP/2014 dated Mar. 7, 2019, 6 pages.
First Office Action from Corresponding Chinese Patent Application No. 201811312211.3, dated Aug. 3, 2021, 27 Pages.
Fuertes M.B., et al., "Host Type I IFN Signals are Required for Antitumor CD8+ T Cell Responses Through CD8α+ Dendritic Cells," Journal of Experimental Medicine, 2011, vol. 208, pp. 2005-2016.
Gabrilovich D.I., et al., "Myeloid-Derived-Suppressor Cells as Regulators of the Immune System," Nat. Rev. Immunol, Mar. 2009, vol. 9, No. 3, pp. 162-174.
Gahery-Segard H., et al., "Multiepitopic B- And T-Cell Responses Induced in Humans by a Human Immunodeficiency Virus Type 1 Lipopeptide Vaccine," American Society For Microbiology, Journal Of Virology, Feb. 2000, vol. 74, No. 4, pp. 1694-1703.
Gandhapudi S.K., et al., "Antigen Priming With Enantiospecific Cationic Lipid Nanoparticles Induces Potent Antitumor CTL Responses Through Novel Induction Of A Type I IFN Response," Journal of Immunology, May 3, 2019, vol. 202, pp. 3524-3536, Retrieved from URL: http://www.jimmunol.org/contenU202/12/3524.
Glick D., "Methods of Biochemical Analysis," Cancer Biology Research Laboratory, Stanford University Medical Center, Stanford, California, 1988, vol. 33, pp. 337-462.
Gluck R., et al., "Biophysical Validation of Epaxal Berna, a Hepatitis A Vaccine Adjuvanted with Immunopotentiating Reconstituted Influenza Virosomes (IRIV)," Developments in Biologicals, 2000, vol. 103, 12 Pages.
Gold J.S., et al. "A Single Heteroclitic Epitope Determines Cancer Immunity After Xenogeneic Dna Immunization Against A Tumor Differentiation Antigen," The Journal of Immunology, 2003, 170. 10, pp. 5188-5194.
Grabowska et al., "Identification of Promiscuous Hpv16-Derived T Helper Cell Epitopes for Therapeutic Hpv Vaccine Design," International Journal of Cancer, 2015, vol. 136, No. 1, pp. 212-224, XP055497833.

Greenfield I., et al., "Human Papillomavirus 16 E7 Protein is Associated with the Nuclear Matrix," Proceedings of the National Academy of Sciences of the United States of America, Dec. 1991, vol. 88, pp. 11217-11221.
Gregoriadis G., et al., "Vaccine Entrapment in Liposomes," Methods, 1999, vol. 19, pp. 156-162.
Gregoriadis G., "Immunological Adjuvants: A Role for Liposomes," Immunology Today, The School of Pharmacy, University of London, 1990, vol. 11, No. 3, pp. 89-97.
Hamley I.W., "Self-Assembly of Amphiphilic Peptides," Soft Matter, 2011, vol. 7, pp. 4122-4138.
Hasegawa A., et al., "Nasal Immunization With Diphtheria Toxoid Conjugated-CD52 Core Peptide Induced Specific Antibody Production In Genital Tract Of Female Mice," American Journal Of Reproductive Immunology, 2002, vol. 48, pp. 305-311.
Hassan C., et al., "Naturally Processed Non-Canonical HLA-A*02:01 Presented Peptides," The Journal of Biological Chemistry, 2015, vol. 290, No. 5, pp. 2593-2603, XP055497822.
Helmby H., et al., "Interleukin-1 Plays A Major Role In The Development Of Th2-Mediated Immunity," European Journal Of Immunology, WHILEY-VCH Verlag Gmbh & Co., 2004, vol. 34, pp. 3674-3681.
Holten-Anderson L., et al., "Combination of the Cationic Surfactant Dimethyl Dioctadecyl Ammonium Bromide and Synthetic Mycobacterial Cord Factor as an Efficient Adjuvant for Tuberculosis Subunit Vaccines," Infection and Immunity, Mar. 2004, vol. 72, No. 3, pp. 1608-1617.
Hultner L., "In Activated Mast Cells, IL-1 Up-Regulates The Production Of Several Th2-Related Cytokines Including IL-9," The American Association Of Immunologists, The Journal Of Immunology, 2000, vol. 164, pp. 5556-5563.
Immordino et al., "Stealth Liposomes: Review of the Basic Science, Rationale, and Clinical Applications, Existing and Potential," International Journal of Nanomedicine, 2006, vol. 1, No. 03, pp. 297-315.
Inaba K., et al., "Generation Of Large Numbers Of Dendritic Cells From Mouse Bone Marrow Cultures Supplemented With Granulocyte/Macrophage Colony-Stimulating Factor," Journal Of Experimental Medicine, The Rockefeller University Press, Dec. 1992, vol. 176, pp. 1693-1702.
International Preliminary Report on Patentability for International Application No. PCT/US2009/040500, dated Oct. 28, 2010, 6 Pages.
International Preliminary Report on Patentability for International Application No. PCT/US2013/045578, dated Dec. 24, 2014, 7 Pages.
International Preliminary Report on Patentability for International Application No. PCT/US2013/061132, dated Apr. 2, 2015, 10 Pages.
International Preliminary Report on Patentability for International Application No. PCT/US2017/055119, dated Apr. 18, 2019, 16 Pages.
International Search Report and Written Opinion for International Application No. PCT/US2009/040500, dated Jun. 4, 2009, 7 Pages.
International Search Report and Written Opinion for International Application No. PCT/US2013/045578, dated Nov. 25, 2013, 9 Pages.
International Search Report and Written Opinion for International Application No. PCT/US2013/061132, dated Dec. 30, 2013, 12 Pages.
International Search Report and Written Opinion for International Application No. PCT/US2017/055119, dated Mar. 7, 2018, 23 Pages.
International Search Report and Written Opinion for International Application No. PCT/US2021/060337, dated Feb. 14, 2022, 7 Pages.
International Preliminary Report on Patentability for International Application No. PCT/US2008/057678, dated Sep. 22, 2009, 5 Pages.
International Preliminary Report on Patentability for International Application No. PCT/US2012/054786, dated Mar. 20, 2014, 6 Pages.

(56) References Cited

OTHER PUBLICATIONS

International Preliminary Report on Patentability for International Application No. PCT/US2016/061829, dated May 24, 2018, 15 Pages.
International Preliminary Report on Patentability for International Application No. PCT/US2017/055348, dated Apr. 18, 2019, 6 Pages.
International Preliminary Report on Patentability for International Application No. PCT/US2018/064060, dated Jun. 18, 2020, 7 Pages.
International Search Report and Written Opinion for International Application No. PCT/US2008/057678, dated Apr. 20, 2009, 6 Pages.
International Search Report and Written Opinion for International Application No. PCT/US2012/054786, dated Nov. 15, 2012, 8 Pages.
International Search Report and Written Opinion for International Application No. PCT/US2016/061829, dated Feb. 24, 2017, 18 Pages.
International Search Report and Written Opinion for International Application No. PCT/US2017/055348, dated Jan. 5, 2018, 8 Pages.
International Search Report and Written Opinion for International Application No. PCT/US2018/064060, dated Apr. 30, 2019, 9 Pages.
International Search Report for International Application No. PCT/US2008/057678, dated Apr. 20, 2009, 3 Pages.
International Search Report for International Application No. PCT/US2009/040500, dated Jun. 4, 2009, 2 Pages.
Ishida T., et al., "Defective Function Of Langerhans Cells In Tumor-Bearing Animals is the Result of Defective Maturation from Hemopoietic Progenitors," The American Association Of Immunologists, The Journal Of Immunology, 1998, vol. 161, pp. 4842-4851.
Iwaoka S.,et al., "Cationic Liposomes Induce Apoptosis Through p38 MAP-kinase-caspase-8-Bid Pathway in Macrophage-like RAW 264.7 Cells", Journal of Leukocyte Biology, Jan. 2006, vol. 79, pp. 184-191, XP008117765.
Jacob A., et al., "Convergence of Signaling Pathways on the Activation of ERK in B Cells," The Journal of Biological Chemistry, The American Society for Biochemistry and Molecular Biology Incorporated, Jun. 28, 2002, vol. 277, No. 26, pp. 23420-23426.
Jiao X., et al, "Modulation of Cellular Immune Response Against Hepatitis C Virus Nonstructural Protein 3 by Cationic Liposome Encapsulated DNA Immunization," Hepatology, Feb. 2003, vol. 37, No. 2, pp. 452-460.
Jisho: "Kojien," Japanese Dictionary, Third Edition, Iwanami Shoten, 1983, 1 Page.
Johnson G.L., et al, "Mitogen-activated Protein Kinase Pathways Mediated by ERK, JNK, and p38 Protein Kinases," Science, Dec. 6, 2002, vol. 298, pp. 1911-1912.
Jones C.A., et al., "Vaccination Strategies to Prevent Genital Herpes and Neonatal Herpes Simplex Virus (HSV) Disease," Herpes, 2004, vol. 11, pp. 12-17.
Kabarowski J.H.S., et al., "Lysophospatidylcholine As A Ligand For The Immunoregulatory Receptor G2A," Science, Department Of Microbiology, Immunology, And Molecular Genetics, Department Of Cancer Biology, Lerner Research Institute, Cleveland, Ohio, Jul. 27, 2001, vol. 293, 06 pages.
Kahn J.O., et al., "Clinical and Immunologic Responses to Human Immunodeficiency Virus (HIV) Type 1SF2 GP120 Subunit Vaccine Combined with MF59 Adjuvant with or without Muramyl Tripeptide Dipalmitoyl Phosphatidylethanolamine in Non-HIV-Infected Human Volunteers," The Journal of Infectious Diseases, 1994, vol. 170, pp. 1288-1291.
Kanafani Z.A., et al., "Daptomycin: A Rapidly Bactericidal Lipopeptide for the Treatment of Gram-Positive Infections," Experimental Review of Antibacterial Infections, Future Drugs Ltd, 2007, vol. 5, No. 2, pp. 177-184.
Kantengwa S., et al., "Superoxide Anions Induce The Maturation of Human Dendritic Cells," American Journal of Respiratory and Critical Care Medicine, Divisions of Pneumology and Thoracic Surgery, University Hospital, Geneva, Switzerland, Feb. 1, 2003, vol. 167, No. 3, pp. 431-437.
Kenter G.G., et al., "Vaccination Against Hpv-16 Oncoproteins for Vulvar Intraepithelial Neoplasia," The New England Journal of Medicine, Nov. 5, 2009, vol. 361, pp. 1838-1847.
Kim J.J., et al., "CD8 Positive T Cells Influence Antigen-Specific Immune Responses through the expression of Chemokines," Journal Of Clinical Investigation, The American Society For Clinical Investigation, Inc., Sep. 1998, vol. 102, No. 6, pp. 1112-1124.
Kogkopoulou O., et al., "Conditional Up-Regulation of IL-2 Production By p38 MAPK Inactivation Is Mediated By Increased ERKI/2 Activity," Journal of Leukocyte Biology, May 2006, vol. 79, pp. 1052-1060.
Kokkoli E., et al., "Self-assembly and Applications of Biomimetic and Bioactive Peptide-amphiphiles," Soft Matter, 2006, vol. 2, pp. 1015-1024.
Korsholm , "Unravelling the Adjuvant Mechanism of Cationic Liposomes," Statens Serum Institute, Jun. 2006, pp. 15.00-15.30.
Korsholm K.S., et al., "The Adjuvant Mechanism of Dimethyldioctadecyl-ammonium Liposomes," Immunology, Jun. 2007, vol. 121, No. 2, pp. 216-226.
Kranz L.M., et al., "Systemic RNA Delivery to Dendritic Cells Exploits Antiviral Defence for Cancer Immunotherapy," Nature, Jun. 16, 2016, vol. 534, 16 Pages, DOI:10.1038/nature18300, XP055565453.
Li S., et al., "Targeted Delivery of Antisense Oligodeoxynucleotide and Small Interference RNA Into Lung Cancer Cells," Molecular Pharmaceutics, American Chemical Society, 2006, vol. 3, No. 5, pp. 579-588.
Liang M.T., et al., "Encapsulation of Lipopeptides Within Liposomes: Effect of Number of Lipid Chains, Chain Length and Method of Liposome Preparation," International Journal of Pharmaceutics, Elsevier B.V., 2005, vol. 301, pp. 247-254.
Lodoen M.B., et al., "Natural Killer Cells as an Initial Defense Against Pathogens," Current Opinion in Immunology, Elsevier Ltd, 2006, vol. 18, pp. 391-398.
Lonez C., et al., "Cationic Liposomal Lipids: From Gene Carriers to Cell Signaling," Progress in Lipid Research, 2008, vol. 47, pp. 340-347.
Lucas W., et al., "Viral Capsids and Envelopes: Structure and Function," Encyclopedia of Life Sciences (ELS), John Wiley & Sons, 2010, pp. 1-7.
MacKay C.R., "Chemokines: Immunology's High Impact Factors," Nature Immunology, Feb. 2001, vol. 2, No. 2, pp. 95-101.
Mansour M., et al., "Therapy Of Established B16-f10 Melanoma Tumors By A Single Vaccination Of Ctl/t Helper Peptides In Vaccimax," Journal of Translational Medicine, 2007, vol. 5, No. 20, 8 Pages.
Melief C.J.M., et al., "Effective Therapeutic Anticancer Vaccines Based on Precision Guiding of Cytolytic T Lymphocytes," Blackwell Munksgaard, Immunological Reviews, 2002, vol. 188, pp. 177-182.
Minutello M., et al., "Safety And Immunogenicity Of An Inactivated Subunit Influenza Virus Vaccine Combined With MF59 Adjuvant Emulsion In Elderly Subjects," Immunized For Three Consecutive Influenza Seasons, Vaccine, Elsevier Science Limited, 1999, vol. 17, pp. 99-104.
Moingeon P., et al., "Towards the Rational Design of Th1 Adjuvants," Vaccine, Elsevier Science Limited, 2001, vol. 19, pp. 4363-4372.
Non Final Office Action for Counterpart dated Mar. 5, 2020 for U.S. Appl. No. 16/532,728, 12 Pages.
Non Final Office Action dated Apr. 29, 2022 for U.S. Appl. No. 14/531,469, 12 Pages.
Non-Final Office Action from Counterpart U.S. Appl. No. 15/775,680, dated Apr. 1, 2020, 14 Pages.
Notification of Reason of Rejection of Japanese Application No. JP2017218514, dated Aug. 21, 2018, 13 pages.
Office Action for Canadian Application No. 2885741, dated May 10, 2022, 03 pages.
Office Action for Corresponding Russian Application No. 2015101110, with its English translation, dated Aug. 8, 2017, 06 pages.

(56) References Cited

OTHER PUBLICATIONS

Office Action for Corresponding Russian Application No. 2015101110, with its English translation, dated Mar. 28, 2017, 10 pages.
Office Action for European Application No. 08799629.4, dated Aug. 7, 2012, 4 Pages.
Office Action for European Application No. 08799629.4, dated Jan. 10, 2014, 3 Pages.
Office Action for European Application No. 08799629.4, dated May 17, 2010, 1 Page.
Office Action for European Application No. 08799629.4, dated Apr. 26, 2011, 3 Pages.
Office Action for European Application No. 09733034.4, dated Apr. 16, 2015, 5 Pages.
Office Action for European Application No. 09733034.4, dated Nov. 18, 2016, 4 Pages.
Office Action for European Application No. 12831495.2, dated Dec. 1, 2016, 4 Pages.
Office Action for European Application No. 12831495.2, dated Jun. 6, 2016, 5 Pages.
Office Action for European Application No. 12831495.2, dated May 11, 2017, 4 Pages.
Office Action for European Application No. 13804165.2, dated Mar. 2, 2018, 3 Pages.
Office Action for European Application No. 13804165.2, dated Jul. 5, 2017, 4 Pages.
Office Action for European Application No. 13804165.2, dated May 17, 2018, 3 Pages.
Office Action for European Application No. 13804165.2, dated Sep. 22, 2016, 3 Pages.
Office Action for European Application No. 13804165.2, dated Aug. 23, 2018, 3 Pages.
Office Action for European Application No. 13839199.0, dated Nov. 21, 2016, 4 Pages.
Office Action for European Application No. 13839199.0, dated Jul. 30, 2018, 4 Pages.
Office Action for European Application No. 16865201.4, dated Jul. 16, 2020, 5 Pages.
Office Action for European Application No. 19203293.6, dated Feb. 19, 2021, 4 Pages.
Office Action for European Application No. 19203293.6, dated Dec. 22, 2021, 4 Pages.
Office Action for Taiwanese Application No. TW101133392, with English Translation, dated Jul. 17, 2017, 05 pages.
Office Action from Corresponding Indian Application No. 7544/DELNP/2010, dated Jun. 22, 2017, 10 Pages.
Office Action from Counterpart Brazilian Patent Application. No. PI0910464-0, dated Nov. 6, 2018, and a Brief Summary in English, 5 pages.
Office Action from Counterpart Taiwanese Patent Application. No. 106109798 with English translation, dated Nov. 14, 2017, 09 pages.
Office Action of European Application No. 12831495.2, dated Nov. 17, 2015, 5 pages.
Office Action of Taiwanese Application No. 101133392, dated May 16, 2016, along with an English translation of the Search Report, 8 pages.
Okada N., et al., "Effects of Lipofectin-Antigen Complexes on Major Histocompatibility Complex Class I-Restricted Antigen Presentation Pathway in Murine Dendritic Cells and on Dendritic Cell Maturation," Biochimica et Biophysica Acta, Elsevier Science, 2001, vol. 1527, pp. 97-101.
Oliveira L.M.F.D., et al., "Design of Immune Responses and Anti-Tumor Potential of an HPV16 E6E7 Multi-Epitope Vaccine," PLoS One, 2015, vol. 10, No. 9: e0138686, 13 Pages.
Padron-Regalado E., "Vaccine for SARS-CoV-2: Lessons from Other Coronavirus Strains," Infectious Diseases and Therapeutics, 2020, vol. 9, pp. 255-274.
Perales M., et al., "Phase I/II Study of GM-CSF DNA as an Adjuvant for a Multipeptide Cancer Vaccine in Patients with Advanced Melanoma," Molecular Therapy, Dec. 2008, vol. 16, No. 12, pp. 2022-2029.

Pialoux G.D., et al., "Lipopeptides Induce Cell-Mediated Anti-HIV Immune Responses In Seronegative Volunteers," Lippincott Williams & Wilkins, Inc., Official Journal Of The International Of AIDS, Jul. 6, 2001, vol. 15, No. 10, pp. 1239-1249.
Pierre Y., et al., "Liposome-Mediated DNA Immunisation via the Subcutaneous Route," Journal of Drug Targeting, Taylor & Francis Ltd, 2003, vol. 11, No. 8-10, pp. 555-563.
Radu C.G., et al., "T Cell Chemotaxis to Lysophosphatidylcholine through the G2A Receptor," Proceedings of the National Academy of Sciences, The National Academy of Sciences of The USA, Jan. 6, 2004, vol. 101, No. 1, pp. 245-250.
Rao P.E., et al., "Differentiation and Expansion of T Cells with Regulatory Function from Human Peripheral Lymphocytes by Stimulation in the Presence of TGF-B," The Journal of Immunology, The American Association of Immunologists, Inc., 2005, vol. 174, pp. 1446-1455.
Restriction Requirement from Counterpart dated Jan. 7, 2020 for U.S. Appl. No. 15/775,680, 09 Pages.
Riemer A.B., et al., "A Conserved E7-Derived Cytotoxic T Lymphocyte Epitope Expressed On Human Papillomavirus-16 Transformed HLA-A2+ Human Epithelial Cancers," The Journal Of Biological Chemistry, Sep. 17, 2010, vol. 285, No. 38, pp. 29608-29622, XP055207597.
Robinson J.H., et al., "Palmitic Acid Conjugation of a Protein Antigen Enhances Major Histocompatibility Complex Class II-Restricted Presentation to T Cells," Immunology, 1992, vol. 76, pp. 593-598.
Rock K.L., et al., "Natural Endogenous Adjuvants," Spriner Semin Immunology, 26, 2005, pp. 231-246.
Ross T.M., "A Trivalent Virus-like Particle Vaccine Elicits Protective Immune Responses against Seasonal Influenza Strains in Mice and Ferrets," PloS one, e6032, Jun. 24, 2009, vol. 4, No. 6, pp. 1-11.
Rughetti A., et al., "Transfected Human Dendritic Cells to Induce Antitumor Immunity," Gene Therapy, Sep. 2000, vol. 7. No. 17, pp. 1458-1466.
Santin A.D., et al., "Induction of Human Papillomavirus-Specific CD4 + and CDS+ Lymphocytes by E7-Pulsed Autologous Dendritic Cells in Patients with Human Papillomavirus Type 16- and 18-Positive Cervical Cancer," Journal of Virology, Jul. 1999, vol. 73, No. 7, pp. 5402-5410.
Sato N., et al., "CC Chemokine Receptor (CCR) 2 Is Required For Langhans Cell Migration And Localization Of T Helper Cell Type 1 (Th1)—Inducing Dendritic Cells: Absence Of CCR2 Shifts The Leishmania Major-Resistant Phenotype To A Susceptible State Dominated By Th2 Cytokines, B Cell Outgrowth, And Sustained Neutrophilic Inflammation," Journal Of Experimental Medicine, The Rockefeller University Press, Jul. 17, 2000, vol. 192, No. 2, pp. 205-218.
Schroeder M.A., et al., "Pegylated Murine GM-CSF Increases Myeloid Derived Suppressor Cells In Vivo," Blood, 2011, vol. 118, No. 21, p. 2967, ISSN: 0003513278.
Shimizu T., et al., "Antitumor Activity, Mitogenicity, and Lethal Toxicity of Chemical Synthesized Monosaccharide Analog of Lipid A," J. Pharmacobiodyn, 1988, vol. 11, No. 7, pp. 512-518.
Shinozaki Y., et al., "Tumor-specific Cytotoxic T Cell Generation And Dendritic Cell Function Are Differentially Regulated By Interleukin 27 During Development Of Anti-tumor Immunity," International Journal of Cancer, 2009, vol. 124, No. 6, pp. 1372-1378.
Sinha P., et al., "Cross-Talk Between Myeloid-Derived Suppressor Cells and Macrophages Subverts Tumor Immunity Toward a Type 2 Response," The Journal of Immunology, 2007, vol. 179, pp. 977-983.
Song Y.K., et al., "Free Liposomes Enhance the Transfection Activity of DNA/Lipid Complexes in Vivo by Intravenous Administration," Biochimica et Biophysica Acta, 1998, vol. 1372, pp. 141-150.
Sprott G.D., et al., "Activation of Dendritic Cells by Liposomes Prepared from Phosphatidylinositol Mannosides from *Mycobacterium bovis* Bacillus Calmette-Guerin and Adjuvant Activity In Vivo," Infection and Immunity, Sep. 2004, vol. 72, No. 9, pp. 5235-5246.
Steller M.A., et al., "Cell-Mediated Immunological Responses in Cervical and Vaginal Cancer Patients Immunized with a Lipidated

(56) References Cited

OTHER PUBLICATIONS

Epitope of Human Papillomavirus Type 16 E7," Clinical Cancer Research, Sep. 1998, vol. 4, pp. 2103-2109.
Sumida S.M., et al., "Recruitment and Expansion of Dendritic Cells In Vivo Potentiate the Immunogenicity of Plasmid DNA Vaccines," The Journal of Clinical Investigation, USA, Nov. 2004, vol. 114, No. 9, pp. 1334-1342.
Sun W.Q., et al., "Stability of Dry Liposomes in Sugar Glasses," Biophysical Journal, Apr. 1996, vol. 70, pp. 1769-1776.
Supplementary European Search Report for European Application No. 13804165.2, dated Jan. 22, 2016, 07 Pages.
Taiwan Search Report for Taiwanese Application No. 107143751, dated Jul. 27, 2022, 2 Pages, with translation.
Takaoka A., et al., "Integration of interferon—Alpha/Beta Signaling to P53 Responses in Tumor Suppression and Antiviral Defense," Nature, Jul. 31, 2003, vol. 424, pp. 516-523.
The Notice of Reasons for Rejection of Counterpart Japanese Patent Application No. 2019-518245, dated Oct. 26, 2021, Along With an English Translation, 14 Pages.
Third Examiner's Report from Corresponding Canadian Patent Application No. 2,876,656, dated Mar. 25, 2021, 5 Pages.
Tindle R., et al., "NCBI Blast Search Teaching Sequence 43," Genback, U.S. Pat. No. 6,183,745, 2001, 1 Page.
Tobiume K., et al., "ASK1 Is Required For Sustained Activations Of JNL/p38 MAP Kinases And Apoptosis," EMBO Reports, European Molecular Biology Organization, 2001, vol. 2, No. 3, pp. 222-228.
Toledo H., et al., "A Phase I Clinical Trial of a Multi-Epitope Polypeptide TAB9 Combined with Montanide ISA720 Adjuvant in Non-HIV-1 Infected Human Volunteers," Vaccine, Elsevier Science Ltd, 2001, vol. 19, pp. 4328-4336.
Translation of Notification of Reason for Rejection from Corresponding Japanese Patent Application No. 2013-217819, dated Jan. 10, 2017, 7 Pages.
"Transplantation," Supplement 1, 2010, vol. 90, No. 2S, pp. 519-2687, 1 Page, ISSN: 0003513279.
Tsang K.Y., et al., "Identification and Characterization of Enhancer Agonist Human Cytotoxic T-cell Epitopes of The Human Papillomavirus Type 16 (Hpv16) E6/E7," Vaccine, 2017, vol. 35, pp. 2605-2611.
Uemura A., et al., "Induction Of Immune Responses Against Glycosphingolipid Antigens: Comparison Of Antibody Responses In Mice Immunized With Antigen Associated With Liposomes Prepared From Various Phospholipids," Journal Of Veterinary Medical Science, 2005, vol. 67, No. 12, pp. 1197-1201.
United States Patent and Trademark Office, Offic Action for U.S. Appl. No. 11/121,840, dated Sep. 7, 2007, 6 Pages.
United States Patent and Trademark Office, Office Action for U.S. Appl. No. 11/121,840, dated Jun. 4, 2007, 5 Pages.
Vangasseri D.P., "Immunostimulation of Dendritic Cells by Cationic Liposomes," Molecular Membrane Biology, Taylor and Francis, GB, Sep. 1, 2006, vol. 23, No. 5, pp. 385-395, DOI: 10.1080/09687860600790537, ISSN 0968-7688, XP008137311.
Varypataki E.M., et al., "Cationic Liposomes Loaded With a Synthetic Long Peptide and Poly(L:C): a Defined Adjuvanted Vaccine for Induction Of Antigen-Specific T Cell Cytotoxicity," The AAPS Journal, Jan. 2015, vol. 17, No. 1, pp. 216-226.
Vasievich E. A., et al., "Enantiospecific Adjuvant Activity of Cationic Lipid DOTAP in Cancer Vaccine", Cancer Immunology, Immunotherapy, May 2011, vol. 60, No. 5, Abstract Only, 1 Page.
Vasievich E.A., et al., "Enantiospecific Adjuvant Activity of Cationic Lipid DOTAP In Cancer Vaccine," Cancer Immunology, Immunotherapy, May 1, 2011, vol. 60, No. 5, pp. 629-638, DOI:10.1007/s00262-011-0970-1, ISSN 0340-7004, XP055057926.
Vasievich E.A., et al., "Trp2 Peptide Vaccine Adjuvanted With O-dotap Inhibits Tumor Growth In An Advanced Melanoma Model," Division of Molecular Pharmaceutics, 2012, vol. 9, pp. 261-268.
Vautier-Giongo C., et al., "Effects Of Interactions On The Formation Of Mixed Micelles Of 1.2-diheptaoyl-sn-glycero-3-phosphocholine With Sodiumdodecyl Sulfate And Dodecyltrimethylemmonuium Bromide," Journal of Colloid and Interface Science 282, 2005, pp. 149-155.
Verheul A.F.M., et al., "Monopalmitic Acid-Peptide Conjugates Induce Cytotoxic T Cell Responses Against Malarial Epitopes: Importance of Spacer Amino Acids," Journal of Immunological Methods, Elsevier Science B.V., 1995, vol. 182, pp. 219-226.
Vogel F.R., et al., "A Compendium of Vaccine Adjuvants and Excipients," Pharmaceutical biotechnology, 1995, vol. 6, 89 Pages.
Vogel F.R., "Improving Vaccine Performance With Adjuvants," Clinical Infectious Diseases, Infectious Diseases Society Of America, 2000, vol. 30, Suppl. 3, pp. S266-S270.
Wang H., et al., "Potential Involvement Of Monocyte Chemoattractant Protein (MCP)-1/CCL2 In IL-4-Mediated Tumor Immunity Through Inducing Dendritic Cell Migration Into The Draining Lymph Nodes," International Immunopharmacology, Elsevier Science B.V, 2003, vol. 03, pp. 627-642.
Wang L., et al., "Lysophosphatidylcholine-Induced Surface Redistribution Regulates Signaling Of The Murine G Protein-Coupled Receptor G2A," Molecular Biology Of The Cell, The American Society For Cell Biology, May 2005, vol. 16, pp. 2234-2247.
Wang R-F., et al., "Enhancement of Antitumor Immunity By Prolonging Antigen Presentation on Dendritic Cells," Nature Biotechnology, Nature Publishing Group, Feb. 2002, vol. 20, pp. 149-154.
Welters M.J.P., et al., "Induction of Tumor-Specific CD4+ and CD8+ T-Cell Immunity in Cervical Cancer Patients by a Human Papillomavirus Type 16 E6 and E7 Long Peptides Vaccine," Clinical Cancer Research, Jan. 1, 2008, vol. 14, No. 1, pp. 178-187.
Whitmore M., et al., "LPD Lipopolyplex Initiates A Potent Cytokine Response And Inhibits Tumor Growth," Gene Therapy, Stockton Press, 1999, vol. 6, pp. 1867-1875.
Wrapp D., et al., "Cryo-EM Structure of the 2019-nCOV Spike in the Prefusion Conformation," Science, Mar. 13, 2020, vol. 367, pp. 1260-1263.
Xiao X., et al., "HLA-A, HLA-B, HLA-DRB1 Polymorphisms and Risk of Cervical Squamous Epithelial Cell Carcinoma: A Population Study in China," Asian Pacific Journal of Cancer Prevention, 2013, vol. 14, No. 7, pp. 4427-4433, XP055497830.
Yamshchikov G.V., et al., "Evaluation Of Peptide Vaccine Immunogenicity In Draining Lymph Nodes And Peripheral Blood Of Melanoma Patients," International Journal of Immunology, Wiley-Liss, Inc., 2001, vol. 92, pp. 703-711.
Yan W., et al., "Mechanism of Adjuvant Activity of Cationic Liposome: Phosphorylation of A MAP Kinase, ERK and Induction of Chemokines," Molecular Immunology, 2007, vol. 44, pp. 3672-3681.
Yao T., et al., "Integrated Basic Chemistry for Geo Science," Naniing University Press, 2007, pp. 410-421.
Yao Y., et al., "HPV-16 E6 and E7 Protein T Cell Epitopes Prediction Analysis Based on Distributions of HLA-A Loci Across Populations: An in Silico Approach," Vaccine, 2013, vol. 31, No. 18, pp. 2289-2294, XP055497828.
Yasuda K., et al., "Endosomal Translocation of Vertebrate DNA Activates Dendritic Cells via TLR9—Dependent and Independent Pathways," The Journal of Immunology, 2005, vol. 174, pp. 6129-6136.
Yoo J.K., et al., "IL-18 Induces Monocyte Chemotactic Protein-1 Production in Macrophages Through the Phosphatidylinositol 3-Kinase/Akt and MEK/ERK1/2 Pathways," The Journal of Immunology, The American Association of Immunologists Incorporated, 2005, vol. 175, pp. 8280-8286.
Yoshimura T., et al., "Human Monocyte Chemoattractant Protein-1 (MCP-1), Full Length cDNA Cloning, Expression In Mitogen-Stimulated Blood Mononuclear Leukocytes, and Sequence Similarity To Mouse Competence Gene JE," Federation of European Biochemical Societies, Elsevier Science Publishers B.V., Feb. 1989, vol. 244, No. 2, pp. 487-493.
Yotsumoto S., et al., "Endosomal Translocation of CpG-Oligodeoxynucleotides Inhibits DNA-PKcs—Dependent IL-10 Production in Macrophages," The Journal of Immunology, 2008, vol. 180, pp. 809-816.

(56) References Cited

OTHER PUBLICATIONS

Yu H., et al., "Novel Chlamydia Muridarum T Cell Antigens Induce Protective Immunity Against Lung and Genital Tract Infection in Murine Models," The Journal of Immunology, 2009, vol. 182, pp. 1602-1608.

Yu J.J., et al., "Regulation and Phenotype of an Innate Th1 Cell: Role of Cytokines and the P38 Kinase Pathway," The Journal of Immunology, The American Association of Immunologists, 2003, vol. 171, pp. 6112-6118.

Zaks K., et al., "Efficient Immunization and Cross-Priming by Vaccine Adjuvants Containing TLR3 or TLR9 Agonists Complexed to Cationic Liposomes," The Journal of Immunology, 2006, vol. 176, pp. 7335-7345.

Zhang H., et al., "English Translation of Specification of CN111217918," European Patent Office, 2020, 85 pages.

Zhang H., et al., "Stress-Induced Inhibition of ERK1 and ERK2 by Direct Interaction With p38 MAP Kinase," The Journal of Biological Chemistry, The American Society for Biochemistry and Molecular BiologyInc, Mar. 9, 2001, vol. 276, No. 10, pp. 6905-6908.

Zhang L., et al., "Converting Peptides into Drug Leads by Lipidation," Current Medicinal Chemistry, 2012, vol. 19, No. 11, pp. 1602-1618, ISSN 0929-8673.

Zhao L.-J., et al., "Interferon Alpha Regulates MAPK and STAT1 Pathways in Human Hepatoma Cells," Virology Journal, Apr. 6, 2011, vol. 8, No. 157, pp. 1-7.

Zitvogel L., et al., "Type I Interferons in Anticancer Immunity," Nature Reviews Immunology, Jul. 2015, vol. 15, pp. 405-414.

U.S. Non-Final Office Action in U.S. Appl. No. 14/531,469, dated Mar. 10, 2023, 13 pages.

U.S. Non-Final Office Action in U.S. Appl. No. 16/532,613, dated Mar. 17, 2023, 120 pages.

U.S. Non-Final Office Action in U.S. Appl. No. 16/899,763, dated Mar. 16, 2023, 52 pages.

Lonez et al., Cationic Lipids Activate Intracellular Signaling Pathways, Advanced Drug Delivery Reviews, 2012, 64(15), pp. 1749-1758.

Office Action for Korean Patent Application No. 10 2019 7012979, dated Oct. 25, 2022, 11 Pages (with English translation).

Office Action for Taiwan Patent Application No. 107143751, dated Aug. 1, 2022, 13 Pages (with English translation).

Wang, et al., Classification of Human Leukocyte Antigen (HLA) Supertypes, Immunoinformatics, Methods in Molecular Biology, 2014, vol. 1184, pp. 309-317.

\* cited by examiner

VACCINE COMPOSITIONS AND METHODS OF USE

INCORPORATION OF SEQUENCE LISTING

The material in the accompanying sequence listing is hereby incorporated by reference into this application. The accompanying sequence listing text file, name PDS_16_1045WO_US_CON_Sequence_Listing, was created on Aug. 6, 2019, and is 3 kb. The file can be accessed using Microsoft Word on a computer that uses Windows OS.

TECHNICAL FIELD

Despite an increasing amount of research and interest in the field of immunology, there is currently a lack of vaccines that are adequately effective against various infectious pathogens or diseases such as malaria, HIV, hepatitis C, influenza, and tuberculosis. For example, current influenza vaccines induce antibodies against two main surface proteins from the virus, hemagglutinin and neuraminidase. Thus, current influenza vaccines only effectively protect against infection by strains of the virus that express versions of these proteins present in the vaccine. However, these two surface proteins frequently change as a consequence of mutations and re-assortment. Accordingly, influenza vaccines must be reformulated each year to contain the hemagglutinin and neuraminidase surface proteins of the newly formed virus strains.

Moreover, influenza virus infections, especially pandemic strains such as H1N1 and H5N1, represent an ever increasing global health risk. The risk is significantly greater in the elderly and in persons with chronic diseases, often leading to higher mortality rates in these patient populations. Vaccination has been a successful means of controlling disease. However, due to the potentially limited availability of vaccines in a pandemic due to current methods of production, and also the limited efficacy in the elderly, more efficient production methods as well as more effective influenza vaccines are being sought. Influenza and other vaccines against infectious pathogens that will be effective against multiple strains of the pathogens, referred to as "universal vaccines" are actively being sought. Furthermore, efficacy of the current influenza vaccines varies significantly. Due to the health risks associated with pandemic strains of influenza in particular, safe and effective adjuvants that are compatible with influence antigens and which can enable effective dose sparing of current antigen stocks are also being actively sought.

Pathogens such as malaria, HIV, hepatitis C, and tuberculosis are intracellular, requiring the induction of strong cellular immunity (including cytotoxic responses (CTL)) to remove the infected cells. It is well established that the development of antibody responses can be stimulated by traditional adjuvants such as alum and Freund's adjuvant. It is also well established that some adjuvants can elicit T-cell responses when formulated with T-cell epitope peptides. However, most current adjuvants lack the ability, when formulated with whole proteins or with viral or bacterial subunit vaccines (as well as live and attenuated virus vaccines), to internalize and process the antigens for presentation via both MHC Class I and Class II to induce both cellular and antibody mixed immune responses. It is now understood that many vaccines will need to stimulate both humoral and cellular immune responses to be adequately effective. Co-generation of MHC class I restricted CD8+T cells is now known to be essential for vaccines aimed at viral and other intracellular infections. Accordingly, an obstacle exists for developing vaccines that are based on attenuated pathogens and non-living vectors containing recombinant antigens, as it is necessary for such agents to access both MHC class I- and class II-restricted pathways of antigen processing.

In particular, methods to improve the protective efficacy of subunit and live pathogen vaccines against various bacterial and viral pathogens by enabling "cross-presentation" involving the processing of an exogenous protein through the class I and class II processing pathways are highly desirable. Enabling of "cross-presentation" through the class I and class II processing pathways yields both antibody and T-cell responses.

BACKGROUND AND SUMMARY OF THE INVENTION

As described above, immunity has been difficult to induce against the proteins found in emerging strains of influenza, such as those in H5N1 viruses that cause avian flu. It is commonly believed that difficulties occur partly because of the existence of memory cells that can recognize annual, but not new, viral strains. A primary response is required, however, to protect against newly emerging virus strains as they are more antigenically distinct from the annual influenza strains. Such a primary response usually requires the addition of an adjuvant.

Addition of adjuvants (e.g., MF59, AS03, or aluminum salts) to influenza vaccines increases antibody titers and persistence. However, these approaches do not provide cross-reactivity to distinct subtypes of the virus. CD8+ T cells recognize less variable parts of the virus and could provide a more cross-reactive response that could be induced by new vaccines.

There has been a recent shift in the focus of influenza vaccine development, as well as vaccines for other pathogens, towards the generation of memory CD8+ T cells that may be able to provide more cross-reactive protection. As mentioned above, the antigens that CD8+ T cells recognize are found in less variable portions of the virus. Several approaches have been attempted. For example, peptides recognized by CD8+ T cells have been combined with a lipid moiety, Pam-2-Cys, that activates a TLR on DCs to prime protective CD8+ T cells. This vaccine generates protective CD8+ T cells that migrate to the lung when administered via intranasal delivery.

CD8+ T cells are specific to detect agents, such as viruses, that invade the cytoplasm, and the requirements for presentation of antigen to CD8+ T cells differ from those for the CD4 helper T-cells. Antigens are transported to the cell surface by molecules encoded in the MHC. Internalized antigen is carried to the cell surface by MHC class II, which promotes activation of CD4+ T-cells. In contrast, endogenous antigen reaches the cell surface by MHC class I, which activates CD8+ T-cells. To activate cytotoxic T-cells (CD8+), antigen internalized by DCs must cross to the MHC class I pathway before reappearing on the cell surface, a process known as cross-presentation, for which specific subsets of DCs are specialized. Adjuvant systems that are able to activate antigen cross-presentation are actively being sought and are essential in the development of new generation vaccines.

Several other infections, such as hepatitis, HIV, and malaria, for example, exist for which antibodies provide insufficient protection. In these cases, both humoral immunity, mediated by antibodies, and cell-mediated immunity, which depends on cytotoxic T cells or T cells that activate immune cells by means of cytokines, may be required for effective protection.

Dendritic cells (DCs) are the primary antigen-presenting cells in the initiation of T cell responses, and are therefore a major target for adjuvant use. In the presence of an infection, signals are sent to DCs directly by pattern-recognition receptors (PRRs) for microbial constituents, and indirectly by inflammatory cytokines released by other innate immune cells that recognize microbial constituents. These signals induce maturation of the DCs and their migration to secondary lymphoid organs where they are able to interact with and activate naïve T cells. DC maturation involves increased processing of microbial proteins and their presentation to T cells on major histocompatibility complex (MHC) molecules.

Some adjuvants have been demonstrated to activate signals that induce T helper cell ($T_H1$) responses, characterized by IFNγ-producing T helper cells that activate antimicrobial effects at the effector site. Adjuvants such as the saponins drive $T_H1$ responses and are believed to work by inducing IL-12 in DCs. Aluminum salts, however, do not directly induce signaling through TLRs and do not stimulate IL-12 production by DCs. Instead, aluminum-based adjuvants have been found to drive $T_H2$ responses.

Adjuvants work by various mechanisms and the ability to effect cross-presentation is ultimately dependent on the adjuvant's mechanism. Some mechanisms by which an adjuvant effect is achieved include retention of the antigen locally at the site of injection to produce a slow-release depot effect, thus enabling sustained release of the antigen to the antigen presenting cells. Adjuvants can also at as chemoattractants to attract cells of the immune system to the antigen depot and subsequently stimulate such cells to elicit immune responses. The most commonly used adjuvant to date has been Alum (Aluminum hydroxide and aluminum phosphate). Most adjuvants including Alum are effective in only enhancing the antibody responses to antigens. Adjuvants such as MPL can activate antibody responses, and when formulated with T-cell epitope peptides, have also been demonstrated to elicit CTL responses.

As described above, although some adjuvants such as the cationic lipids and MPL can elicit T-cell responses when formulated with peptides, the use of peptide fragments rather than whole antigens is a severe limitation because different peptide fragments are recognized by the T cells of different individuals. As a result, a very large number of different fragments would have to be identified and included in such a vaccine. In addition, the ability of peptides to elicit protective antibody responses is known to be weak and non-existent with several peptides.

A promising approach is to induce CTL to internal proteins such as NP which are highly conserved among different viruses. Hemagglutinin (HA) T cell epitopes also show less variation than antibody epitopes. However, existing inactivated vaccines like Fluzone consist of mostly HA protein and yet do not generate significant CD8 T cell responses.

The killing of infected cells by both CTLs and $T_H1$ cells is reported to be effective in clearing an infection due to an intracellular pathogen. However, in certain cases, (e.g. infection of the liver by the hepatitis B virus), IFNγ-producing CD8+ T cells offer more effective protection because the virus can be cleared with minimal host cell death. Similarly, IFNγ-producing CD8+ T cells are shown to be associated with protection in individuals vaccinated with the RTS, S malaria vaccine. This vaccine contains a protein from the parasite fused to a surface protein from the hepatitis B virus.

It is reported that both humoral and cell-mediated immunity targeting multiple antigens expressed at different stages of the parasite's lifecycle are required for protection against malaria infection. The adjuvant system used in the most successful malarial vaccine is AS02, a combination adjuvant preparation that contains both a saponin adjuvant component and the TLR agonist MPL formulated in a particulate system. Notably, both the saponin and MPL adjuvants together were required to induce cross presentation and hence a modest level of protection in immunized individuals. In contrast, however, vaccines using the same antigen with aluminum hydroxide and MPL (AS04) or in an oil-in-water emulsion (AS03) induced high levels of antibody but failed to protect against infection.

Although live attenuated viral and bacterial vaccines can activate all arms of the immune system, adjuvants have so far not reached this goal. By combining adjuvants, such as aluminum salts with MPL, or by using prime-boost strategies with DNA and then viral or bacterial vectors, both humoral and cell-mediated responses can potentially be activated. However, such multiple adjuvant systems are complex and have the potential for formulation and safety difficulties.

Therefore, there exists a need for new vaccine compositions that effectively induce broadly cross-protective immunity to different subtypes of a pathogen, for example an influenza virus. Moreover, new and effective methods of treating and preventing disease, such as those caused by bacteria, viruses, and fungi are also very desirable. Accordingly, the present disclosure provides vaccine compositions and method of using the compositions that exhibit desirable properties and provide related advantages for cross-presentation of one or more antigens and wherein a humoral and/or a cellular immune response is achieved.

The present disclosure provides vaccine compositions comprising at least one adjuvant and at least one antigen, wherein the adjuvant is a cationic lipid. The disclosure also provides methods of treating a disease in a mammal, methods of preventing a disease in a mammal, and methods of A method of effecting antigen cross presentation to induce a humoral immune response and a cellular immune response in a mammal utilizing the vaccine compositions. Cross presentation of various antigens can be achieved by formulating the specific antigens with cationic lipids possessing adjuvant properties.

The vaccine compositions and methods according to the present disclosure provide several advantages compared to other compositions and methods in the art. First, the vaccine compositions can induce broadly cross-protective immunity to different subtypes of influenza, as well as development of a universal influenza vaccine that can provide protection against multiple influenza strains.

Second, the vaccine compositions demonstrate strong increases in both humoral and cell-mediated responses and can provide a simple adjuvant platform for developing a new generation of simple vaccines that do not require adjuvant combinations or viral vectors. This approach to eliciting "cross-presentation" in the development of anti-viral and anti-bacterial vaccines could provide a novel and cost effective approach to the development of vaccines that provide improved protection and cure of various diseases.

Third, the influenza vaccine compositions can provide a new approach to developing a universal influenza vaccine without the need for the use of multiple T-cell epitope peptides due to the enhanced cellular CD8+ T-cell response to the HA protein and resulting "cross-reactivity" among strains in which the CD8 T-cell epitopes are known to be conserved.

The following numbered embodiments are contemplated and are non-limiting:

1. A vaccine composition comprising at least one adjuvant and at least one antigen, wherein the adjuvant is a cationic lipid.

2. The vaccine composition of clause 1 wherein the cationic lipid is a non-steroidal cationic lipid.

3. The vaccine composition of clause 1 or clause 2 wherein the cationic lipid is selected from the group consisting of DOTAP, DOTMA, DOEPC, and combinations thereof.

4. The vaccine composition of any one of clauses 1 to 3 wherein the cationic lipid is DOTAP.

5. The vaccine composition of any one of clauses 1 to 3 wherein the cationic lipid is DOTMA.

6. The vaccine composition of any one of clauses 1 to 3 wherein the cationic lipid is DOEPC.

7. The vaccine composition of any one of clauses 1 to 6 wherein the adjuvant is an enantiomer of the cationic lipid.

8. The vaccine composition of clause 7 wherein the enantiomer is purified.

9. The vaccine composition of clause 7 or clause 8 wherein the enantiomer is R-DOTAP or S-DOTAP.

10. The vaccine composition of clause 7 or clause 8 wherein the enantiomer is R-DOTAP.

11. The vaccine composition of clause 7 or clause 8 wherein the enantiomer is S-DOTAP.

12. The vaccine composition of clause 7 or clause 8 wherein the enantiomer is R-DOTMA or S-DOTMA.

13. The vaccine composition of clause 7 or clause 8 wherein the enantiomer is R-DOTMA.

14. The vaccine composition of clause 7 or clause 8 wherein the enantiomer is S-DOTMA.

15. The vaccine composition of clause 7 or clause 8 wherein the enantiomer is R-DOEPC or S-DOEPC.

16. The vaccine composition of clause 7 or clause 8 wherein the enantiomer is R-DOEPC.

17. The vaccine composition of clause 7 or clause 8 wherein the enantiomer is S-DOEPC.

18. The vaccine composition of any one of clauses 1 to 17 wherein one or more antigens is a protein-based antigen.

19. The vaccine composition of any one of clauses 1 to 17 wherein one or more antigens is a peptide-based antigen.

20. The vaccine composition of any one of clauses 1 to 19 wherein one or more antigens is selected from the group consisting of a viral antigen, a fungal antigen, a bacterial antigen, and a pathogenic antigen.

21. The vaccine composition of any one of clauses 1 to 19 wherein one or more antigens is a viral antigen.

22. The vaccine composition of any one of clauses 1 to 19 wherein one or more antigens is a fungal antigen.

23. The vaccine composition of any one of clauses 1 to 19 wherein one or more antigens is a bacterial antigen.

24. The vaccine composition of any one of clauses 1 to 19 wherein one or more antigens is a pathogenic antigen.

25. The vaccine composition of any one of clauses 1 to 24 wherein at least one antigen is an antigen from a conserved region of the pathogen.

26. The vaccine composition of clause 24 wherein the pathogenic antigen is a synthetic or recombinant antigen.

27. The vaccine composition of any one of clauses 1 to 20 wherein at least one antigen is selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), KSSMHGDTPTLHEYMLDLQPETT (SEQ. ID. NO: 6), KSSLLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), and KSSKVPRNQDWL (SEQ. ID. NO: 11).

28. The vaccine composition of any one of clauses 1 to 20 wherein at least one antigen is selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

29. The vaccine composition of any one of clauses 1 to 20 wherein the antigens are gp100 (KVPRNQDWL [SEQ. ID. No. 8]) and TRP2 (SYVDFFVWL [SEQ. ID. No. 9]).

30. The vaccine composition of any one of clauses 1 to 20 wherein the antigen is RAHYNIVTF (SEQ. ID. NO: 1).

31. The vaccine composition of any one of clauses 1 to 20 wherein the antigen is GQAEPDRAHYNIVTF (SEQ. ID. NO: 2).

32. The vaccine composition of any one of clauses 1 to 20 wherein the antigen is KSSGQAEPDRAHYNIVTF (SEQ. ID. NO: 3).

33. The vaccine composition of any one of clauses 1 to 20 wherein the antigen is YMLDLQPETT (SEQ. ID. NO: 4).

34. The vaccine composition of any one of clauses 1 to 20 wherein the antigen is KSSYMLDLQPETT (SEQ. ID. NO: 5).

35. The vaccine composition of any one of clauses 1 to 20 wherein the antigen is KSSMHGDTPTLHEYMLDLQPETT (SEQ. ID. NO: 6).

36. The vaccine composition of any one of clauses 1 to 20 wherein the antigen is KSSLLMGTLGIVCPICSQKP (SEQ. ID. NO: 7).

37. The vaccine composition of any one of clauses 1 to 20 wherein the antigen is KVPRNQDWL (SEQ. ID. NO: 8).

38. The vaccine composition of any one of clauses 1 to 20 wherein the antigen is SYVDFFVWL (SEQ. ID. NO: 9).

39. The vaccine composition of any one of clauses 1 to 20 wherein the antigen is KYICNSSCM (SEQ. ID. NO: 10).

40. The vaccine composition of any one of clauses 1 to 20 wherein the antigen is KSSKVPRNQDWL (SEQ. ID. NO: 11).

41. The vaccine composition of any one of clauses 1 to 40 wherein at least one antigen is selected from the group consisting of a lipoprotein, a lipopeptide, and a protein or peptide modified with an amino acid sequence having an increased hydrophobicity or a decreased hydrophobicity.

42. The vaccine composition of any one of clauses 1 to 41 wherein one or more antigens is a lipidated antigen or an antigen modified to increase hydrophobicity of the antigen.

43. The vaccine composition of any one of clauses 1 to 42 wherein at least one antigen is a modified protein or peptide.

44. The vaccine composition of any one of clauses 1 to 43 wherein the modified protein or peptide is bonded to a hydrophobic group.

45. The vaccine composition of any one of clauses 1 to 44 wherein the modified protein or peptide bonded to a hydrophobic group further comprises a linker sequence between the antigen and the hydrophobic group.

46. The vaccine composition of clause 45 wherein the hydrophobic group is a palmitoyl group.

47. The vaccine composition of any one of clauses 1 to 46 wherein at least one antigen is an unmodified protein or peptide.

48. The vaccine composition of any one of clauses 1 to 47 wherein the vaccine composition is a universal vaccine.

49. The vaccine composition of any one of clauses 1 to 48 wherein the vaccine composition is an anti-viral vaccine.

50. The vaccine composition of any one of clauses 1 to 48 wherein the vaccine composition is an anti-fungal vaccine.

51. The vaccine composition of any one of clauses 1 to 48 wherein the vaccine composition is an anti-bacterial vaccine.

52. The vaccine composition of any one of clauses 1 to 48 wherein the vaccine composition is an influenza vaccine.

53. The vaccine composition of clause 52 wherein the influenza vaccine is a universal influenza vaccine.

54. The vaccine composition of clause 52 or clause 53 wherein the influenza vaccine comprises a glycoprotein antigen found on the surface of an influenza virus.

55. The vaccine composition of clause 54 wherein the antigen is a hemagglutinin antigen.

56. The vaccine composition of clause 55 wherein the hemagglutinin antigen comprises an epitope region $HA_{518-526}$.

57. The vaccine composition of clause 55 wherein the influenza vaccine is a neuraminidase subunit vaccine.

58. The vaccine composition of any one of clauses 52 to 57 wherein the influenza vaccine is an H3N2 vaccine.

59. The vaccine composition of any one of clauses 52 to 57 wherein the influenza vaccine is an N1N1 vaccine.

60. The vaccine composition of any one of clauses 52 to 57 wherein the influenza vaccine is a Brisbane vaccine.

61. The vaccine composition of any one of clauses 52 to 57 wherein the influenza vaccine is an H1N1 vaccine.

62. The vaccine composition of any one of clauses 52 to 61 wherein the influenza vaccine comprises one or more protein antigens from one or more influenza viruses.

63. The vaccine composition of any one of clauses 52 to 62 wherein the influenza vaccine comprises an inactivated virus (e.g. an inactivated whole virus).

64. The vaccine composition of any one of clauses 52 to 61 wherein the influenza vaccine comprises an attenuated virus.

65. The vaccine composition of any one of clauses 52 to 61 wherein the influenza vaccine comprises a disrupted virus.

66. The vaccine composition of any one of clauses 52 to 61 wherein the influenza vaccine comprises a recombinant virus.

67. The vaccine composition of any one of clauses 1 to 67 wherein the vaccine composition is capable of inducing a humoral immune response.

68. The vaccine composition of clause 67 wherein the humoral immune response is an antibody response. 69. The vaccine composition of any one of clauses 1 to 68 wherein the vaccine composition is capable of inducing a humoral immune response against a conserved region of a pathogen.

70. The vaccine composition of any one of clauses 1 to 69 wherein the vaccine composition is capable of inducing a cellular immune response. 71. The vaccine composition of clause 70 wherein the cellular immune response is a T cell response.

72. The vaccine composition of clause 71 wherein the T cell response is a CD 8+ T cell response.

73. The vaccine composition of any one of clauses 1 to 72 wherein the vaccine composition is capable of inducing a cellular immune response against a conserved region of a pathogen.

74. The vaccine composition of any one of clauses 1 to 73 wherein the vaccine composition is capable of inducing a humoral immune response and a cellular immune response in the patient.

75. The vaccine composition of any one of clauses 1 to 74 wherein the vaccine composition is capable of cross-presentation of one or more antigens.

76. The vaccine composition of any one of clauses 1 to 75 wherein the vaccine composition generates a humoral immune response and a cellular immune response.

77. The vaccine composition of any one of clauses 1 to 76 wherein the vaccine composition induces an immune response in a mammal by activating the mitogen-activated protein (MAP) kinase signaling pathway.

78. The vaccine composition of clause 77 wherein the MAP kinase signaling pathway is activated by stimulating at least one of extracellular signal-regulated kinase ("ERK")-1, ERK-2, and p38.

79. The vaccine composition of any one of clauses 1 to 78 wherein the vaccine composition enhances functional antigen-specific CD8+ T lymphocyte response in a mammal.

80. The vaccine composition of clause 79 wherein the mammal is a human.

81. A method of treating a disease in a mammal, said method comprising the step of administering an effective amount of a vaccine composition to the mammal, wherein the vaccine composition comprises at least one adjuvant and at least one antigen, and wherein the adjuvant is a cationic lipid.

82. The method of clause 81 wherein the disease is a pathogenic disease.

83. The method of clause 81 or clause 82 wherein the disease is caused by multiple strains of a pathogen.

84. The method of any one of clauses 81 to 83 wherein the disease is influenza.

85. The method of any one of clauses 81 to 84 wherein the method induces a humoral immune response in the mammal.

86. The method of clause 85 wherein the humoral immune response is an antibody response.

87. The method of clause 85 or clause 86 wherein the humoral immune response is against a conserved region of a pathogen.

88. The method of any one of clauses 81 to 87 wherein the method induces a cellular immune response in the mammal.

89. The method of clause 88 wherein the cellular immune response is a T cell response.

90. The method of clause 89 wherein the T cell response is a CD 8+ T cell response.

91. The method of any one of clauses 88 to 90 wherein the cellular immune response is against a conserved region of a pathogen.

92. The method of any one of clauses 88 to 91 wherein the method induces a humoral immune response and a cellular immune response in the mammal.

93. The method of any one of clauses 88 to 92 wherein the cationic lipid is a non-steroidal cationic lipid.

94. The method of any one of clauses 88 to 93 wherein the cationic lipid is selected from the group consisting of DOTAP, DOTMA, DOEPC, and combinations thereof.

95. The method of any one of clauses 88 to 94 wherein the cationic lipid is DOTAP.

96. The method of any one of clauses 88 to 94 wherein the cationic lipid is DOTMA.

97. The method of any one of clauses 88 to 94 wherein the cationic lipid is DOEPC.

98. The method of any one of clauses 88 to 97 wherein the adjuvant is an enantiomer of the cationic lipid.

99. The method of clause 98 wherein the enantiomer is purified.

100. The method of clause 98 or clause 99 wherein the enantiomer is R-DOTAP or S-DOTAP.

101. The method of clause 98 or clause 99 wherein the enantiomer is R-DOTAP.

102. The method of clause 98 or clause 99 wherein the enantiomer is S-DOTAP.

103. The method of clause 98 or clause 99 wherein the enantiomer is R-DOTMA or S-DOTMA.

104. The method of clause 98 or clause 99 wherein the enantiomer is R-DOTMA.

105. The method of clause 98 or clause 99 wherein the enantiomer is S-DOTMA.

106. The method of clause 98 or clause 99 wherein the enantiomer is R-DOEPC or S-DOEPC.

107. The method of clause 98 or clause 99 wherein the enantiomer is R-DOEPC.

108. The method of clause 98 or clause 99 wherein the enantiomer is S-DOEPC.

109. The method of any one of clauses 81 to 109 wherein one or more antigens is a protein-based antigen.

110. The method of any one of clauses 81 to 109 wherein one or more antigens is a peptide-based antigen.

111. The method of any one of clauses 81 to 110 wherein one or more antigens is selected from the group consisting of a viral antigen, a fungal antigen, a bacterial antigen, and a pathogenic antigen.

112. The method of any one of clauses 81 to 110 wherein one or more antigens is a viral antigen.

113. The method of any one of clauses 81 to 110 wherein one or more antigens is a fungal antigen.

114. The method of any one of clauses 81 to 110 wherein one or more antigens is a bacterial antigen.

115. The method of any one of clauses 81 to 110 wherein one or more antigens is a pathogenic antigen.

116. The method of any one of clauses 81 to 115 wherein at least one antigen is an antigen from a conserved region of the pathogen.

117. The method of clause 115 or clause 116 wherein the pathogenic antigen is a synthetic or recombinant antigen.

118. The method of any one of clauses 81 to 117 wherein at least one antigen is selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), KSSMHGDTPTLHEYMLDLQPETT (SEQ. ID. NO: 6), KSSLLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), and KSSKVPRNQDWL (SEQ. ID. NO: 11).

119. The method of any one of clauses 81 to 117 wherein at least one antigen is selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

120. The method of any one of clauses 81 to 117 wherein the antigens are gp100 (KVPRNQDWL [SEQ. ID. No. 8]) and TRP2 (SYVDFFVWL [SEQ. ID. No. 9]).

121. The method of any one of clauses 81 to 117 wherein the antigen is RAHYNIVTF (SEQ. ID. NO: 1).

122. The method of any one of clauses 81 to 117 wherein the antigen is GQAEPDRAHYNIVTF (SEQ. ID. NO: 2).

123. The method of any one of clauses 81 to 117 wherein the antigen is KSSGQAEPDRAHYNIVTF (SEQ. ID. NO: 3).

124. The method of any one of clauses 81 to 117 wherein the antigen is YMLDLQPETT (SEQ. ID. NO: 4).

125. The method of any one of clauses 81 to 117 wherein the antigen is KSSYMLDLQPETT (SEQ. ID. NO: 5).

126. The method of any one of clauses 81 to 117 wherein the antigen is KSSMHGDTPTLHEYMLDLQPETT (SEQ. ID. NO: 6).

127. The method of any one of clauses 81 to 117 wherein the antigen is KSSLLMGTLGIVCPICSQKP (SEQ. ID. NO: 7).

128. The method of any one of clauses 81 to 117 wherein the antigen is KVPRNQDWL (SEQ. ID. NO: 8).

129. The method of any one of clauses 81 to 117 wherein the antigen is SYVDFFVWL (SEQ. ID. NO: 9).

130. The method of any one of clauses 81 to 117 wherein the antigen is KYICNSSCM (SEQ. ID. NO: 10).

131. The method of any one of clauses 81 to 117 wherein the antigen is KSSKVPRNQDWL (SEQ. ID. NO: 11).

132. The method of any one of clauses 81 to 131 wherein at least one antigen is selected from the group consisting of a lipoprotein, a lipopeptide, and a protein or peptide modified with an amino acid sequence having an increased hydrophobicity or a decreased hydrophobicity.

133. The method of any one of clauses 81 to 132 wherein one or more antigens is a lipidated antigen or an antigen modified to increase hydrophobicity of the antigen.

134. The method of any one of clauses 81 to 133 wherein at least one antigen is a modified protein or peptide.

135. The method of clause 134 wherein the modified protein or peptide is bonded to a hydrophobic group.

136. The method of clause 134 or clause 135 wherein the modified protein or peptide bonded to a hydrophobic group further comprises a linker sequence between the antigen and the hydrophobic group.

137. The method of clause 136 wherein the hydrophobic group is a palmitoyl group.

138. The method of any one of clauses 81 to 137 wherein at least one antigen is an unmodified protein or peptide.

139. The method of any one of clauses 81 to 138 wherein the vaccine composition is a universal vaccine.

140. The method of any one of clauses 81 to 138 wherein the vaccine composition is an anti-viral vaccine.

141. The method of any one of clauses 81 to 138 wherein the vaccine composition is an anti-fungal vaccine.

142. The method of any one of clauses 81 to 138 wherein the vaccine composition is an anti-bacterial vaccine.

143. The method of any one of clauses 81 to 138 wherein the vaccine composition is an influenza vaccine.

144. The method of any one of clauses 81 to 138 wherein the influenza vaccine is a universal influenza vaccine.

145. The method of clause 143 or clause 144 wherein the influenza vaccine comprises a glycoprotein antigen found on the surface of an influenza viruses.

146. The method of clause 145 wherein the antigen is a hemagglutinin antigen.

147. The method of clause 146 wherein the hemagglutinin antigen comprises an epitope region $HA_{518-526}$.

148. The method of clause 143 or clause 144 wherein the influenza vaccine is a neuraminidase subunit vaccine.

149. The method of any one of clauses 143 to 148 wherein the influenza vaccine is an H3N2 vaccine.

150. The method of any one of clauses 143 to 148 wherein the influenza vaccine is an N1N1 vaccine.

151. The method of any one of clauses 143 to 148 wherein the influenza vaccine is a Brisbane vaccine.

152. The method of any one of clauses 143 to 148 wherein the influenza vaccine is an H1N1 vaccine.

153. The method of any one of clauses 143 to 152 wherein the influenza vaccine comprises one or more protein antigens from one or more influenza viruses.

154. The method of any one of clauses 143 to 153 wherein the influenza vaccine comprises an inactivated virus (e.g. an inactivated whole virus).

155. The method of any one of clauses 143 to 152 wherein the influenza vaccine comprises an attenuated virus.

156. The method of any one of clauses 143 to 152 wherein the influenza vaccine comprises a disrupted virus.

157. The method of any one of clauses 143 to 152 wherein the influenza vaccine comprises a recombinant virus.

158. The method of any one of clauses 81 to 157 wherein the vaccine composition induces an immune response in a mammal by activating the mitogen-activated protein (MAP) kinase signaling pathway.

159. The method of clause 158 wherein the MAP kinase signaling pathway is activated by stimulating at least one of extracellular signal-regulated kinase ("ERK")-1, ERK-2, and p38.

160. The method of any one of clauses 143 to 159 wherein the vaccine composition enhances functional antigen-specific CD8+ T lymphocyte response in a mammal.

161. The method of any one of clauses 81 to 138 wherein the mammal is a human.

162. A method of preventing a disease in a mammal, said method comprising the step of administering an effective amount of a vaccine composition to the mammal, wherein the vaccine composition comprises at least one adjuvant and at least one antigen, and wherein the adjuvant is a cationic lipid.

163. The method of clause 162 wherein the disease is a pathogenic disease.

164. The method of clause 162 or clause 163 wherein the disease is caused by multiple strains of a pathogen.

165. The method of any one of clauses 162 to 164 wherein the disease is influenza.

166. The method of any one of clauses 162 to 165 wherein the method induces a humoral immune response in the mammal.

167. The method of clause 166 wherein the humoral immune response is an antibody response.

168. The method of clause 166 or clause 167 wherein the humoral immune response is against a conserved region of a pathogen.

169. The method of any one of clauses 162 to 168 wherein the method induces a cellular immune response in the mammal.

170. The method of clause 169 wherein the cellular immune response is a T cell response. 171. The method of clause 170 wherein the T cell response is a CD 8+ T cell response.

172. The method of any one of clauses 169 to 171 wherein the cellular immune response is against a conserved region of a pathogen.

173. The method of any one of clauses 162 to 172 wherein the method induces a humoral immune response and a cellular immune response in the mammal.

174. The method of any one of clauses 162 to 173 wherein the cationic lipid is a non-steroidal cationic lipid.

175. The method of any one of clauses 162 to 174 wherein the cationic lipid is selected from the group consisting of DOTAP, DOTMA, DOEPC, and combinations thereof.

176. The method of any one of clauses 162 to 175 wherein the cationic lipid is DOTAP.

177. The method of any one of clauses 162 to 175 wherein the cationic lipid is DOTMA.

178. The method of any one of clauses 162 to 175 wherein the cationic lipid is DOEPC.

179. The method of any one of clauses 162 to 178 wherein the adjuvant is an enantiomer of a cationic lipid.

180. The method of clause 179 wherein the enantiomer is purified.

181. The method of clause 179 or clause 180 wherein the enantiomer is R-DOTAP or S-DOTAP.

182. The method of clause 179 or clause 180 wherein the enantiomer is R-DOTAP.

183. The method of clause 179 or clause 180 wherein the enantiomer is S-DOTAP.

184. The method of clause 179 or clause 180 wherein the enantiomer is R-DOTMA or S-DOTMA.

185. The method of clause 179 or clause 180 wherein the enantiomer is R-DOTMA.

186. The method of clause 179 or clause 180 wherein the enantiomer is S-DOTMA

187. The method of clause 179 or clause 180 wherein the enantiomer is R-DOEPC or S-DOEPC.

188. The method of clause 179 or clause 180 wherein the enantiomer is R-DOEPC.

189. The method of clause 179 or clause 180 wherein the enantiomer is S-DOEPC.

190. The method of any one of clauses 162 to 189 wherein one or more antigens is a protein-based antigen.

191. The method of any one of clauses 162 to 190 wherein one or more antigens is a peptide-based antigen.

192. The method of any one of clauses 162 to 191 wherein one or more antigens is selected from the group consisting of a viral antigen, a fungal antigen, a bacterial antigen, and a pathogenic antigen.

193. The method of any one of clauses 162 to 191 wherein one or more antigens is a viral antigen.

194. The method of any one of clauses 162 to 191 wherein one or more antigens is a fungal antigen.

195. The method of any one of clauses 162 to 191 wherein one or more antigens is a bacterial antigen.

196. The method of any one of clauses 162 to 191 wherein one or more antigens is a pathogenic antigen.

197. The method of any one of clauses 162 to 196 wherein at least one antigen is an antigen from a conserved region of the pathogen.

198. The method of any one of clauses 162 to 197 wherein the pathogenic antigen is a synthetic or recombinant antigen.

199. The method of any one of clauses 162 to 198 wherein at least one antigen is selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), KSSMHGDTPTLHEYMLDLQPETT (SEQ. ID. NO: 6), KSSLLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), and KSSKVPRNQDWL (SEQ. ID. NO: 11).

200. The method of any one of clauses 162 to 198 wherein at least one antigen is selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

201. The method of any one of clauses 162 to 198 wherein the antigens are gp100 (KVPRNQDWL [SEQ. ID. No. 8]) and TRP2 (SYVDFFVWL [SEQ. ID. No. 9]).

202. The method of any one of clauses 162 to 198 wherein the antigen is RAHYNIVTF (SEQ. ID. NO: 1).

203. The method of any one of clauses 162 to 198 wherein the antigen is GQAEPDRAHYNIVTF (SEQ. ID. NO: 2).

204. The method of any one of clauses 162 to 198 wherein the antigen is KSSGQAEPDRAHYNIVTF (SEQ. ID. NO: 3).

205. The method of any one of clauses 162 to 198 wherein the antigen is YMLDLQPETT (SEQ. ID. NO: 4).

206. The method of any one of clauses 162 to 198 wherein the antigen is KSSYMLDLQPETT (SEQ. ID. NO: 5).

207. The method of any one of clauses 162 to 198 wherein the antigen is KSSMHGDTPTLHEYMLDLQPETT (SEQ. ID. NO: 6).

208. The method of any one of clauses 162 to 198 wherein the antigen is KSSLLMGTLGTVCPICSQKP (SEQ. ID. NO: 7).

209. The method of any one of clauses 162 to 198 wherein the antigen is KVPRNQDWL (SEQ. ID. NO: 8).

210. The method of any one of clauses 162 to 198 wherein the antigen is SYVDFFVWL (SEQ. ID. NO: 9).

211. The method of any one of clauses 162 to 198 wherein the antigen is KYICNSSCM (SEQ. ID. NO: 10).

212. The method of any one of clauses 162 to 198 wherein the antigen is KSSKVPRNQDWL (SEQ. ID. NO: 11).

213. The method of any one of clauses 162 to 212 wherein at least one antigen is selected from the group consisting of a lipoprotein, a lipopeptide, and a protein or peptide modified with an amino acid sequence having an increased hydrophobicity or a decreased hydrophobicity.

214. The method of any one of clauses 162 to 213 wherein one or more antigens is a lipidated antigen or an antigen modified to increase hydrophobicity of the antigen.

215. The method of any one of clauses 162 to 213 wherein at least one antigen is a modified protein or peptide.

216. The method of clause 215 wherein the modified protein or peptide is bonded to a hydrophobic group.

217. The method of clause 215 or clause 216 wherein the modified protein or peptide bonded to a hydrophobic group further comprises a linker sequence between the antigen and the hydrophobic group.

218. The method of clause 217 wherein the hydrophobic group is a palmitoyl group.

219. The method of any one of clauses 162 to 218 wherein at least one antigen is an unmodified protein or peptide.

220. The method of any one of clauses 162 to 219 wherein the vaccine composition is a universal vaccine.

221. The method of any one of clauses 162 to 220 wherein the vaccine composition is an anti-viral vaccine.

222. The method of any one of clauses 162 to 219 wherein the vaccine composition is an anti-fungal vaccine.

223. The method of any one of clauses 162 to 219 wherein the vaccine composition is an anti-bacterial vaccine.

224. The method of any one of clauses 162 to 219 wherein the vaccine composition is an influenza vaccine.

225. The method of clause 224 wherein the influenza vaccine is a universal influenza vaccine.

226. The method of clause 224 or clause 225 wherein the influenza vaccine comprises a glycoprotein antigen found on the surface of an influenza viruses.

227. The method of clause 226 wherein the antigen is a hemagglutinin antigen.

228. The method of clause 227 wherein the hemagglutinin antigen comprises an epitope region $HA_{518-526}$.

229. The method of any one of clauses 224 to 228 wherein the influenza vaccine is a neuraminidase subunit vaccine.

230. The method of any one of clauses 224 to 229 wherein the influenza vaccine is an H3N2 vaccine.

231. The method of any one of clauses 224 to 229 wherein the influenza vaccine is an N1N1 vaccine.

232. The method of any one of clauses 224 to 229 wherein the influenza vaccine is a Brisbane vaccine.

233. The method of any one of clauses 224 to 229 wherein the influenza vaccine is an H1N1 vaccine.

234. The method of any one of clauses 224 to 233 wherein the influenza vaccine comprises one or more protein antigens from one or more influenza viruses.

235. The method of any one of clauses 224 to 234 wherein the influenza vaccine comprises an inactivated virus (e.g. an inactivated whole virus).

236. The method of any one of clauses 224 to 233 wherein the influenza vaccine comprises an attenuated virus.

237. The method of any one of clauses 224 to 233 wherein the influenza vaccine comprises a disrupted virus.

238. The method of any one of clauses 224 to 233 wherein the influenza vaccine comprises a recombinant virus.

239. The method of any one of clauses 162 to 238 wherein the vaccine composition induces an immune response in a mammal by activating the mitogen-activated protein (MAP) kinase signaling pathway.

240. The method of clause 240 wherein the MAP kinase signaling pathway is activated by stimulating at least one of extracellular signal-regulated kinase ("ERK")-1, ERK-2, and p38.

241. The method of any one of clauses 162 to 240 wherein the vaccine composition enhances functional antigen-specific CD8+T lymphocyte response in a mammal.

242. The method of any one of clauses 162 to 241 wherein the mammal is a human.

243. A method of effecting antigen cross presentation to induce a humoral immune response and a cellular immune response in a mammal, said method comprising the step of administering an effective amount of a vaccine composition to the mammal, wherein the vaccine composition comprises at least one adjuvant and at least one antigen, and wherein the adjuvant is a cationic lipid.

244. The method of clause 243 wherein the humoral immune response is an antibody response.

245. The method of clause 243 or clause 244 wherein the humoral immune response is against a conserved region of a pathogen.

246. The method of any one of clauses 243 to 245 wherein the cellular immune response is a T cell response.

247. The method of clause 246 wherein the T cell response is a CD 8+ T cell response.

248. The method of any one of clauses 243 to 247 wherein the cellular immune response is against a conserved region of a pathogen.

249. The method of any one of clauses 243 to 248 wherein the cationic lipid is a non-steroidal cationic lipid.

250. The method of any one of clauses 243 to 249 wherein the cationic lipid is selected from the group consisting of DOTAP, DOTMA, DOEPC, and combinations thereof.

251. The method of any one of clauses 243 to 250 wherein the cationic lipid is DOTAP.

252. The method of any one of clauses 243 to 250 wherein the cationic lipid is DOTMA.

253. The method of any one of clauses 243 to 250 wherein the cationic lipid is DOEPC.

254. The method of any one of clauses 243 to 249 wherein the adjuvant is an enantiomer of a cationic lipid.

255. The method of clause 254 wherein the enantiomer is purified.

256. The method of clause 254 or clause 255 wherein the enantiomer is R-DOTAP or S-DOTAP.

257. The method of clause 254 or clause 255 wherein the enantiomer is R-DOTAP.

258. The method of clause 254 or clause 255 wherein the enantiomer is S-DOTAP.

259. The method of clause 254 or clause 255 wherein the enantiomer is R-DOTMA or S-DOTMA.

260. The method of clause 254 or clause 255 wherein the enantiomer is R-DOTMA.

261. The method of clause 254 or clause 255 wherein the enantiomer is S-DOTMA.

262. The method of clause 254 or clause 255 wherein the enantiomer is R-DOEPC or S-DOEPC.

263. The method of clause 254 or clause 255 wherein the enantiomer is R-DOEPC.

264. The method of clause 254 or clause 255 wherein the enantiomer is S-DOEPC.

265. The method of any one of clauses 243 to 264 wherein one or more antigens is a protein-based antigen.

266. The method of any one of clauses 243 to 264 wherein one or more antigens is a peptide-based antigen.

267. The method of any one of clauses 243 to 266 wherein one or more antigens is selected from the group consisting of a viral antigen, a fungal antigen, a bacterial antigen, and a pathogenic antigen.

268. The method of any one of clauses 243 to 266 wherein one or more antigens is a viral antigen.

269. The method of any one of clauses 243 to 266 wherein one or more antigens is a fungal antigen.

270. The method of any one of clauses 243 to 266 wherein one or more antigens is a bacterial antigen.

271. The method of any one of clauses 243 to 266 wherein one or more antigens is a pathogenic antigen.

272. The method of any one of clauses 243 to 271 wherein at least one antigen is an antigen from a conserved region of the pathogen.

273. The method of clause 271 or clause 272 wherein the pathogenic antigen is a synthetic or recombinant antigen.

274. The method of any one of clauses 243 to 273 wherein at least one antigen is selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), KSSMHGDTPTLHEYMLDLQPETT (SEQ. ID. NO: 6), KSSLLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), and KSSKVPRNQDWL (SEQ. ID. NO: 11).

275. The method of any one of clauses 243 to 273 wherein at least one antigen is selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof 276. The method of any one of clauses 243 to 273 wherein the antigens are gp100 (KVPRNQDWL [SEQ. ID. No. 8]) and TRP2 (SYVDFFVWL [SEQ. ID. No. 9]).

277. The method of any one of clauses 243 to 273 wherein the antigen is RAHYNIVTF (SEQ. ID. NO: 1).

278. The method of any one of clauses 243 to 273 wherein the antigen is GQAEPDRAHYNIVTF (SEQ. ID. NO: 2).

279. The method of any one of clauses 243 to 273 wherein the antigen is KSSGQAEPDRAHYNIVTF (SEQ. ID. NO: 3).

280. The method of any one of clauses 243 to 273 wherein the antigen is YMLDLQPETT (SEQ. ID. NO: 4).

281. The method of any one of clauses 243 to 273 wherein the antigen is KSSYMLDLQPETT (SEQ. ID. NO: 5).

282. The method of any one of clauses 243 to 273 wherein the antigen is KSSMHGDTPTLHEYMLDLQPETT (SEQ. ID. NO: 6).

283. The method of any one of clauses 243 to 273 wherein the antigen is KSSLLMGTLGIVCPICSQKP (SEQ. ID. NO: 7).

284. The method of any one of clauses 243 to 273 wherein the antigen is KVPRNQDWL (SEQ. ID. NO: 8).

285. The method of any one of clauses 243 to 273 wherein the antigen is SYVDFFVWL (SEQ. ID. NO: 9).

286. The method of any one of clauses 243 to 273 wherein the antigen is KYICNSSCM (SEQ. ID. NO: 10).

287. The method of any one of clauses 243 to 273 wherein the antigen is KSSKVPRNQDWL (SEQ. ID. NO: 11).

288. The method of any one of clauses 243 to 287 wherein at least one antigen is selected from the group consisting of a lipoprotein, a lipopeptide, and a protein or peptide modified with an amino acid sequence having an increased hydrophobicity or a decreased hydrophobicity.

289. The method of any one of clauses 243 to 288 wherein one or more antigens is a lipidated antigen or an antigen modified to increase hydrophobicity of the antigen.

290. The method of any one of clauses 243 to 289 wherein at least one antigen is a modified protein or peptide.

291. The method of clause 290 wherein the modified protein or peptide is bonded to a hydrophobic group.

292. The method of clause 290 or clause 291 wherein the modified protein or peptide bonded to a hydrophobic group further comprises a linker sequence between the antigen and the hydrophobic group.

293. The method of clause 292 wherein the hydrophobic group is a palmitoyl group.

294. The method of any one of clauses 243 to 293 wherein at least one antigen is an unmodified protein or peptide.

295. The method of any one of clauses 243 to 294 wherein the vaccine composition is a universal vaccine.

296. The method of any one of clauses 243 to 295 wherein the vaccine composition is an anti-viral vaccine.

297. The method of any one of clauses 243 to 295 wherein the vaccine composition is an anti-fungal vaccine.

298. The method of any one of clauses 243 to 295 wherein the vaccine composition is an anti-bacterial vaccine.

299. The method of any one of clauses 243 to 295 wherein the vaccine composition is an influenza vaccine.

300. The method of clause 299 wherein the influenza vaccine is a universal influenza vaccine.

301. The method of clause 299 or clause 300 wherein the influenza vaccine comprises a glycoprotein antigen found on the surface of an influenza viruses.

302. The method of clause 301 wherein the antigen is a hemagglutinin antigen.

303. The method of clause 302 wherein the hemagglutinin antigen comprises an epitope region $HA_{518-526}$.

304. The method of any one of clauses 299 to 303 wherein the influenza vaccine is a neuraminidase subunit vaccine.

305. The method of any one of clauses 299 to 304 wherein the influenza vaccine is an H3N2 vaccine.

306. The method of any one of clauses 299 to 304 wherein the influenza vaccine is an N1N1 vaccine.

307. The method of any one of clauses 299 to 304 wherein the influenza vaccine is a Brisbane vaccine.

308. The method of any one of clauses 299 to 304 wherein the influenza vaccine is an H1N1 vaccine.

309. The method of any one of clauses 299 to 308 wherein the influenza vaccine comprises one or more protein antigens from one or more influenza viruses.

310. The method of any one of clauses 299 to 309 wherein the influenza vaccine comprises an inactivated virus (e.g. an inactivated whole virus).

311. The method of any one of clauses 299 to 308 wherein the influenza vaccine comprises an attenuated virus.

312. The method of any one of clauses 299 to 308 wherein the influenza vaccine comprises a disrupted virus.

313. The method of any one of clauses 299 to 308 wherein the influenza vaccine comprises a recombinant virus.

314. The method of any one of clauses 243 to 313 wherein the vaccine composition induces an immune response in a mammal by activating the mitogen-activated protein (MAP) kinase signaling pathway.

315. The method of clause 314 wherein the MAP kinase signaling pathway is activated by stimulating at least one of extracellular signal-regulated kinase ("ERK")-1, ERK-2, and p38.

316. The method of any one of clauses 243 to 315 wherein the vaccine composition enhances functional antigen-specific CD8+ T lymphocyte response in a mammal.

317. The method of any one of clauses 243 to 316 wherein the mammal is a human.

Figure 1:
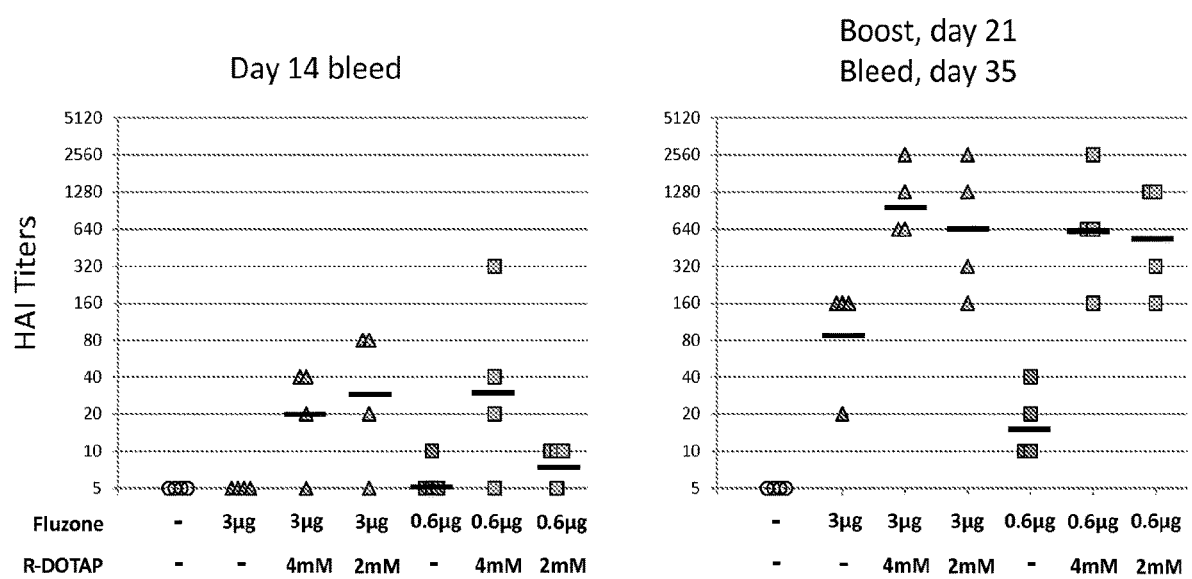
FIG. 1 shows results of a hemagglutination inhibition assay against H3N2 with a commercial influenza vaccine and the cationic lipid-based influenza vaccines.

Various embodiments of the invention are described herein as follows. In one embodiment described herein, a vaccine composition is provided. The vaccine composition comprises at least one adjuvant and at least one antigen, wherein the adjuvant is a cationic lipid.

In another embodiment, a method of treating a disease in a mammal is provided. The method comprises the step of administering an effective amount of a vaccine composition to the mammal, wherein the vaccine composition comprises at least one adjuvant and at least one antigen, and wherein the adjuvant is a cationic lipid.

In yet another embodiment, a method of preventing a disease in a mammal is provided. The method comprises the step of administering an effective amount of a vaccine composition to the mammal, wherein the vaccine composition comprises at least one adjuvant and at least one antigen, and wherein the adjuvant is a cationic lipid.

In yet another embodiment, a method of effecting antigen cross presentation to induce a humoral immune response and a cellular immune response in a mammal is provided. The method comprises the step of administering an effective amount of a vaccine composition to the mammal, wherein the vaccine composition comprises at least one adjuvant and at least one antigen, and wherein the adjuvant is a cationic lipid.

In the various embodiments, the vaccine composition comprises at least one adjuvant and at least one antigen, wherein the adjuvant is a cationic lipid. As used herein, the term "adjuvant" refers to a substance that enhances, augments and/or potentiates a mammal's immune response to an antigen. Doses of the adjuvant are known to those of ordinary skill in the art, as well as those exemplified in PCT/US2008/057678 (Stimulation of an Immune Response by Cationic Lipids), PCT/US2009/040500 (Stimulation of an Immune Response by Enantiomers of Cationic Lipids), both herein incorporated by reference in their entirety.

In some embodiments described herein, the adjuvant is an immunomodulator. As used herein, the term "immunomodulator" refers to an immunologic modifier that enhances, directs, and/or promotes an immune response in a mammal.

In some embodiments described herein, the adjuvant is a nanoparticle. As used herein, the term "nanoparticle" refers to a particle having a size measured on the nanometer scale. As used herein, the "nanoparticle" refers to a particle having a structure with a size of less than about 1,000 nanometers. In some embodiments, the nanoparticle is a liposome.

In some embodiments described herein, the adjuvant is a cationic lipid. As used herein, the term "cationic lipid" refers to any of a number of lipid species which carry a net positive charge at physiological pH or have a protonatable group and are positively charged at pH lower than the pKa.

Cationic lipid-based nanoparticles have been shown to be potent immuno-modifying adjuvants in addition to their ability to act as effective delivery systems, as demonstrated in PCT/US2008/057678 (Stimulation of an Immune Response by Cationic Lipids), PCT/US2009/040500 (Stimulation of an Immune Response by Enantiomers of Cationic Lipids), both herein incorporated by reference in their entirety. The cationic lipid adjuvants in vaccine formulations containing short and long T-cell epitope peptides as expected were demonstrated to elicit superior T-cell immune responses without antibody immune responses.

Suitable cationic lipid according to the present disclosure include, but are not limited to: 3-.beta.[.sup.4N-(.sup.1N,sup.8-diguanidino spermidine)-carbamoyl]cholesterol (BGSC); 3-.beta.[N,N-diguanidinoethyl-aminoethane)-carbamoylicholesterol (BGTC); 15 N,N.sup.1N.sup.2N.sup.3Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2(sperminecarboxamido)ethyl]-N,N-dimethyl-1-propanaminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N'-tetramethyl-N,N'-bis(2-hydroxyethyl)-2,3-diolcoyloxy-1,4-butane-diammonium iodide) (Tfx-50); N-1-(2,3-dioleoyloxy) propyl-N,N,N-trimethyl ammonium chloride (DOTMA) or other N—(N,N-1-dialkoxy)-alkyl-N,N,N-trisubstituted ammonium surfactants; 1,2 dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-.beta.-hydroxyethylammonium) or DORIE (DL-1,2-O-dioleoyl-3-dimethylaminopropyl-.beta.-hydroxyethylammonium) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES), cholesteryl-3.beta.-carboxyl-amido-ethylenetrimethylammonium iodide, 1-dimethylamino-3-trimethylammonio-DL-2-propyl-cholesteryl carboxylate iodide, cholesteryl-3-O-carboxyamidoethyleneamine, cholesteryl-3-.beta.-oxysuccinamido-ethylenetrimethylammonium iodide, 1-dimethylamino-3-trimethylammonio-DL-2-propyl-cholesteryl-3-.beta.-oxysuccinate iodide, 2-(2-trimethylammonio)-ethylmethylamino ethyl-cholesteryl-3-.beta.-oxysuccinate iodide, 3-.beta.-N—(N',N'-dimethylaminoethane) carbamoyl cholesterol (DC-chol), and 3-.beta.-N-(polyethyleneimine)-carbamoylcholesterol; 0,0'-dimyristyl-N-lysyl aspartate (DMKE); O,O'-dimyristyl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-10 dipalmitoyl-sn-glycero-3-ethylphosphocholine (DPEPC); 1,2-distearoyl-sn-glycero-3-ethylphosphocholine (DSEPC); 1,2-dioleoyl-3-trimethylammonium propane (DOTAP); dioleoyl dimethylaminopropane (DODAP); 1,2-palmitoyl-3-trimethylammonium propane (DPTAP); 1,2-distearoyl-3-trimethylammonium propane (DSTAP), 1,2-myristoyl-3-trimethylammonium propane (DMTAP); and sodium dodecyl sulfate (SDS). Furthermore, structural variants and derivatives of the any of the described cationic lipids are also contemplated.

In some embodiment, the cationic lipid is selected from the group consisting of DOTAP, DOTMA, DOEPC, and combinations thereof. In other embodiments, the cationic lipid is DOTAP. In yet other embodiments, the cationic lipid is DOTMA. In other embodiments, the cationic lipid is DOEPC. In some embodiments, the cationic lipid is purified. In other embodiments, the cationic lipid is a non-steroidal cationic lipid.

In some embodiments, the cationic lipid is an enantiomer of a cationic lipid. The term "enantiomer" refers to a stereoisomer of a cationic lipid which is a non-superimposable mirror image of its counterpart stereoisomer, for example R and S enantiomers. In various examples, the enantiomer is R-DOTAP or S-DOTAP. In one example, the enantiomer is R-DOTAP. In another example, the enantiomer is S-DOTAP. In some embodiments, the enantiomer is purified. In various examples, the enantiomer is R-DOTMA or S-DOTMA. In one example, the enantiomer is R-DOTMA. In another example, the enantiomer is S-DOTMA. In some embodiments, the enantiomer is purified. In various examples, the enantiomer is R-DOPEC or S-DOPEC. In one example, the enantiomer is R-DOPEC. In another example, the enantiomer is S-DOPEC. In some embodiments, the enantiomer is purified.

In various embodiments described herein, the composition further comprises one or more antigens. As used herein, the term "antigen" refers to any agent (e.g., protein, peptide, polysaccharide, glycoprotein, glycolipid, nucleic acid, or combination thereof) that, when introduced into a mammal having an immune system (directly or upon expression as in, e.g., DNA vaccines), is recognized by the immune system of the mammal and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR).

In some embodiments, one or more antigens is a protein-based antigen. In other embodiments, one or more antigens is a peptide-based antigen. In various embodiments, one or more antigens is selected from the group consisting of a viral antigen, a bacterial antigen, and a pathogenic antigen. A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In one embodiment, the antigen is a cancer antigen. In one embodiment, the antigen is a viral antigen. In another embodiment, the antigen is a fungal antigen. In another embodiment, the antigen is a bacterial antigen. In various embodiments, the antigen is a pathogenic antigen. In some embodiments, the pathogenic antigen is a synthetic or recombinant antigen.

In some embodiments of the present disclosure, at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), and KSSKVPRNQDWL (SEQ. ID. NO: 11). In one embodiment, at least one antigen comprises the sequence RAHYNIVTF (SEQ. ID. NO: 1). In another embodiment, at least one antigen comprises the sequence GQAEPDRAHYNIVTF (SEQ. ID. NO: 2). In yet another embodiment, at least one antigen comprises the sequence KSSGQAEPDRAHYNIVTF (SEQ. ID. NO: 3). In some embodiments, KSSGQAEPDRAHYNIVTF (SEQ ID. NO: 3) is modified to further comprise a hydrophobic group. In one embodiment, the hydrophobic group is a palmitoyl group.

In other embodiments, at least one antigen comprises the sequence YMLDLQPETT (SEQ. ID. NO: 4). In another embodiment, at least one antigen comprises the sequence KSSYMLDLQPETT (SEQ. ID. NO: 5). In yet another embodiment, KSSYMLDLQPETT (SEQ. ID. NO: 5) is modified to further comprise a hydrophobic group. In one embodiment, the hydrophobic group is a palmitoyl group.

In other embodiments, at least one antigen comprises the sequence KSSMHGDTPTLHEYMLDLQPETT (SEQ. ID. NO: 6). In another embodiment, KSSMHGDTPTLHEYMLDLQPETT (SEQ. ID. NO: 6) is modified to further comprise a hydrophobic group. In one embodiment, the hydrophobic group is a palmitoyl group.

In other embodiments, at least one antigen comprises the sequence KSSLLMGTLGIVCPICSQKP (SEQ. ID. NO: 7). In some embodiments, KSSLLMGTLGIVCPICSQKP (SEQ. ID. NO: 7) is modified to further comprise a hydrophobic group. In one embodiment, the hydrophobic group is a palmitoyl group.

In some embodiments, at least one antigen comprises the sequence KVPRNQDWL (SEQ. ID. NO: 8). In other embodiments, at least one antigen comprises the sequence SYVDFFVWL (SEQ. ID. NO: 9). In yet other embodiments, at least one antigen comprises the sequence KYICNSSCM (SEQ. ID. NO: 10). In another embodiment, at least one antigen comprises the sequence KSSKVPRNQDWL (SEQ. ID. NO: 11). In some embodiments, KSSKVPRNQDWL (SEQ. ID. NO: 11) is modified to further comprise a hydrophobic group. In one embodiment, the hydrophobic group is a palmitoyl group.

In one embodiment, the antigen comprises the sequence selected from the group comprising of gp100 (KVPRNQDWL [SEQ. ID. No. 8]), TRP2 (SYVDFFVWL [SEQ. ID. No.9]), and p53 (KYICNSSCM [SEQ. ID. No. 10]), and combinations thereof.

In one embodiment, the antigens comprise the gp100 sequence 0 (KVPRNQDWL [SEQ. ID. No. 8]) or the TRP2 sequence (SYVDFFVWL [SEQ. ID. No. 9]).

In various embodiments, at least one antigen is selected from the group consisting of a lipoprotein, a lipopeptide, and a protein or peptide modified with an amino acid sequence having an increased hydrophobicity or a decreased hydrophobicity. In some embodiments, one or more antigens is an antigen modified to increase hydrophobicity of the antigen. In one embodiment, at least one antigen is a modified protein or peptide. In some embodiments, the modified protein or peptide is bonded to a hydrophobic group. In other embodiments, the modified protein or peptide bonded to a hydrophobic group further comprises a linker sequence between the antigen and the hydrophobic group. In some embodiments, the hydrophobic group is a palmitoyl group. In yet other embodiments, at least one antigen is an unmodified protein or peptide.

In some embodiments described herein, the vaccine composition is a universal vaccine. As used herein, a "universal" vaccine can protect mammals against a broad range of pathogens, for example a broad range of influenza viruses, and may be effective across multiple strains of a pathogen. Successful development of a universal influenza vaccine could protect mammals against a broad variety of related pathogens rather than just a few. A universal vaccine could potentially be used "off-the-shelf" and could provide some protection against newly emerging pathogens. For example, a universal influenza vaccine influenza virus could provide some protection against newly emerging viruses experts had not identified during worldwide surveillance of these viruses. A universal vaccine could decrease the severity of disease, speed up the ability of the body to clear itself of the pathogen, and reduce the fatality rate of infections until a specific vaccine against that pathogen is available.

In some embodiments described herein, the vaccine composition is an anti-viral vaccine. In some embodiments described herein, the vaccine composition is an anti-fungal vaccine. In some embodiments described herein, the vaccine composition is an anti-bacterial vaccine.

In some embodiments described herein, the vaccine composition is an influenza vaccine. In other embodiments described herein, the influenza vaccine is a universal influenza vaccine. It is demonstrated in the present disclosure that the cationic lipids induce significantly enhanced antibody protection when formulated with the inactivated H3N2, N1N1, and Brisbane strains of the influenza virus. There is a well-established CD8 T cell epitope within hemagglutinin (HA) from the mouse-adapted PR8 strain of virus (H1N1): $HA_{518-576}$, IYSTVASSL (SEQ ID NO:12), $K^d$ restricted. Vaccination with this epitope has been shown to protect mice from lethal infection. This epitope is also shared in the H5N1 virus A/Vietnam/2004 containing full-length hemagglutinin. Immunization with H5 can induce cross-protective CD8 immunity to H1N1 in mice, and thus is considered a good model for cross protective immunity. Effective cross-presentation of the inactivated H5N1 vaccine when formulated with a cationic lipid is shown to lead to significantly enhanced CTL against the CD8 epitope IYSTVASSL (SEQ ID NO:12). The ability of the cationic lipids to cause the exogenous HA proteins from the inactivated virus to be internalized, processed and presented as a peptide via the MHC-class I pathway in addition to presenting the proteins via the MHC class II pathway provides a novel approach to the development of an effective universal influenza vaccine based on recombinant HA proteins or live attenuated and inactivated viruses.

In various embodiments described herein, the influenza vaccine comprises a glycoprotein antigen found on the surface of an influenza virus. In one embodiment, the antigen is a hemagglutinin antigen. In other embodiments, the hemagglutinin antigen comprises an epitope region $HA_{518-526}$.

In various embodiments described herein, the influenza vaccine is a neuraminidase subunit vaccine. In other embodiments described herein, influenza vaccine is an H3N2 vaccine. In yet other embodiments described herein, influenza vaccine is an N1N1 vaccine. In other embodiments described herein, influenza vaccine is a Brisbane vaccine. In yet other embodiments described herein, influenza vaccine is an H1N1 vaccine.

In various embodiments described herein, the influenza vaccine comprises one or more protein antigens from one or more influenza viruses. In other embodiments described herein, the influenza vaccine comprises an inactivated virus (e.g. an inactivated whole virus).

In yet other embodiments described herein, the influenza vaccine comprises an attenuated virus. In some embodiments described herein, the influenza vaccine comprises a disrupted virus. In other embodiments described herein, the influenza vaccine comprises a recombinant virus.

In various embodiments described herein, the vaccine composition is capable of inducing a humoral immune response. As used herein, the term "humoral immune response" is related to the aspect of immunity that is mediated by macromolecules found in extracellular fluids such as secreted antibodies, complement proteins and certain antimicrobial peptides. In some embodiments, the humoral immune response is an antibody response. In various embodiments, the vaccine composition is capable of inducing a humoral immune response against a conserved region of a pathogen.

In various embodiments described herein, the vaccine composition is capable of inducing a cellular immune response. As used herein, the term "cellular immune response" is related to the activation of phagocytes, antigen-specific cytotoxic T-lymphocytes, the release of various cytokines in response to an antigen, and the like. In some embodiments, the cellular immune response is a T cell response. In certain embodiments, the T cell response is a CD 8+ T cell response. In various embodiments, the vaccine composition is capable of inducing a cellular immune response against a conserved region of a pathogen.

In various embodiments described herein, the vaccine composition is capable of effecting antigen cross presentation to induce a humoral immune response and a cellular immune response in the patient. In certain embodiments, the vaccine composition is capable of cross-presentation of one or more antigens. In other embodiments, the vaccine composition generates a humoral immune response and a cellular immune response.

In various embodiments described herein, the vaccine composition induces an immune response in a mammal by activating the mitogen-activated protein (MAP) kinase signaling pathway. Induction of an immune response by adjuvants such as cationic lipids are described, for example, in PCT/US2008/057678 (WO/2008/116078; "Stimulation of an Immune Response by Cationic Lipids") and PCT/US2009/040500 (WO/2009/129227; "Stimulation of an Immune Response by Enantiomers of Cationic Lipids"), the entire disclosures of both incorporated herein by reference. In some embodiments, the MAP kinase signaling pathway is activated by stimulating at least one of extracellular signal-regulated kinase ("ERK")-1, ERK-2, and p38. In other embodiments, the composition enhances functional antigen-specific CD8+ T lymphocyte response. The term "mammal" is well known to those of skill in the art. In one embodiment, the mammal is a human.

In one embodiment described herein, a method of treating a disease in a mammal is provided. The method comprises comprising the step of administering an effective amount of a vaccine composition to the mammal, wherein the vaccine composition comprises at least one adjuvant and at least one antigen, and wherein the adjuvant is a cationic lipid. The previously described embodiments of the vaccine composition are applicable to the method of treating a disease in a mammal described herein. In some embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse. In one embodiment, the method is a prophylactic treatment.

In some embodiments, the disease is a pathogenic disease. In other embodiments, the disease is caused by multiple strains of a pathogen. In certain embodiments, the disease is influenza.

In various embodiments, the method induces a humoral immune response in the mammal. In some embodiments, the humoral immune response is an antibody response.

In other embodiments, the humoral immune response is against a conserved region of a pathogen.

In various embodiments, the method induces a cellular immune response in the mammal. In some embodiments, the cellular immune response is a T cell response. Ion other embodiments, the T cell response is a CD 8+ T cell response. In certain embodiments, the cellular immune response is against a conserved region of a pathogen. In other embodiments, the method induces a humoral immune response and a cellular immune response in the mammal.

In various embodiments, the mammal is a human. In some embodiments, the administration activates an immune response via the MAP kinase signaling pathway in cells of the immune system of the mammal. In various embodiments, the MAP kinase signaling pathway is activated by stimulating at least one of ERK-1, ERK-2, and p38.

In other embodiments, the immune response activates cytotoxic T lymphocytes in the mammal. In one embodiment, the cytotoxic T lymphocytes are CD8+ T cells. In another embodiment, the administration enhances functional antigen-specific CD8+ T lymphocyte response. In yet another embodiment, the immune response activates an antibody response in the mammal. In other embodiments, the immune response activates interferon-gamma (IFN-a) in the mammal.

In one embodiment described herein, a method of preventing a disease in a mammal is provided. The method comprises comprising the step of administering an effective amount of a vaccine composition to the mammal, wherein the vaccine composition comprises at least one adjuvant and at least one antigen, and wherein the adjuvant is a cationic lipid. The previously described embodiments of the vaccine composition and the method of treating a disease in a mammal are applicable to the method of preventing a disease in a mammal described herein.

In one embodiment described herein, a method of effecting antigen cross presentation to induce a humoral immune response and a cellular immune response in a mammal is provided. The method comprises the step of administering an effective amount of a vaccine composition to the mammal, wherein the vaccine composition comprises at least one adjuvant and at least one antigen, and wherein the adjuvant is a cationic lipid. The previously described embodiments of the vaccine composition, the method of treating a disease in a mammal, and the method of preventing a disease in a mammal are applicable to the method of effecting antigen cross presentation to induce a humoral immune response and a cellular immune response in a mammal described herein.

EXAMPLE 1

Formulation of Influenza Vaccine

Sterile water for injection (WFI) or a buffer was used in all liposome preparation procedures. In the present example, R-DOTAP was used as an exemplary cationic lipid. Liposomes used these studies were made using lipid films. Lipid films were made in glass vials by (1) dissolving the lipids in an organic solvent such as chloroform, and (2) evaporating the chloroform solution under a steady stream of dry nitrogen gas. Traces of organic solvent were removed by keeping the films under vacuum overnight. The lipid films were then hydrated by adding the required amount of WFI or buffer to make a final concentration of 4 mM or 8 mM R-DOTAP cationic lipid. The suspensions were then extruded to a size of 200 nm and stored at 4° C. Other cationic lipids and methods used in general liposome preparation that are well known to those skilled in the art may also be used.

A commercial influenza vaccine formulation containing three influenza antigens B Brisbane, A/California/07/2009 (H1N1) A/Perth/16/2009 (H3N2) was diluted to 60 µg/ml or 12 µg/ml in PBS and then mixed 1:1 v/v with 8 mM or 4 mM R-DOTAP or PBS to produce 30 and 611 g/ml in PBS, with 4 mM DOTAP, or 2 mM DOTAP, or PBS. Mixing was performed by pipetting up and down, no emulsion was created. Solution was slightly turbid, but transparent, typical of DOTAP formulations. No precipitate was visible

EXAMPLE 2

Evaluation of the Protective Potency of a Cationic Lipid-Based Influenza Vaccine: Protective Hemagglutination Inhibition Assay Against A/Perth/16/2009 (H3N2

C57BL/6J mice were injected subcutaneously in the shaved flank with 100 ul to deliver a final dose of 3 µg or 0.6 µg of the antigen in either PBS, 4 mM R-DOTAP or 2 mM R-DOTAP. The mice were injected on day 0, then again with the identical formulation on day 21. Tail vein bleeds were performed on days 14 and 35.

Serum was stored frozen at −80° C. prior to testing. Samples were coded with respect to the treatment groups. A Hemagglutination inhibition assay was performed against the viruses A/Perth/16/2009 (H3N2) to quantify the anti-influenza antibody induction and resulting protective efficacy of the vaccines.

Four mice were tested per group:
1. Naïve
2. 3 ug+PBS
3. 3 ug+4 mM R-DOTAP
4. 3 ug+2 mM R-DOTAP
5. 0.6 ug+PBS
6. 0.6 ug+4 mM R-DOTAP
7. 0.6 ug+2 mM R-DOTAP The results are shown in FIG. 1. After the first injection (day 14 bleed), the commercial vaccine demonstrated no protective antibody production against the H3N2 virus.

In contrast, the cationic lipid-based vaccine however demonstrated a significant increase in HAI titers. After injection 2 (day 35 bleed), the high antigen dose vaccine shows about an 8-10 fold increase in antibody induction potency with high or low amounts of R-DOTAP. After injection 2 (day 35 bleed), the low antigen dose vaccine demonstrated about a 40-fold increase in antibody induction potency with either of the vaccine formulations containing the high or low amounts of R-DOTAP. The low dose antigen vaccine with R-DOTAP increased potency about 8-fold compared to the high antigen dose commercial vaccine.

EXAMPLE 3

Evaluation of the Protective Potency of a Cationic Lipid-Based Influenza Vaccine: Protective Hemagglutination Inhibition Assay Against Pandemic Influenza Strain A/California/07/2009 (H1N1)

C57BL/6J mice were injected subcutaneously in the shaved flank with 100 µl to deliver a final dose of 3 µg or 0.6 µg of the antigen in either PBS, 4 mM R-DOTAP or 2 mM R-DOTAP. The mice were injected on day 0, then again with the identical formulation on day 21. Tail vein bleeds were performed on days 14 and 35.

Serum was stored frozen at −80° C. prior to testing. Samples were coded with respect to the treatment groups. A Hemagglutination inhibition assay was performed against the virus A/California/07/2009 (H1N1) to quantify the antibody induction and protective efficacy of the vaccines.

Figure 2:
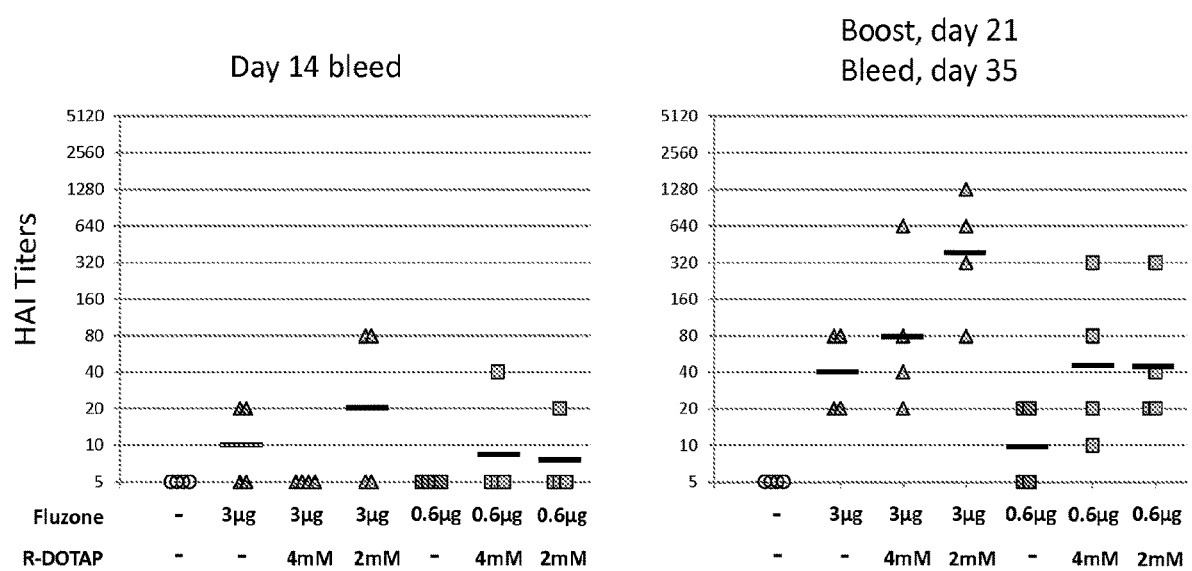
FIG. 2 shows results of a hemagglutination inhibition assay against H1N1 with a commercial influenza vaccine and the cationic lipid-based influenza vaccines.

Four mice were tested per group:
1. Naive
2. 3 ug+PBS
3. 3 ug+4 mM R-DOTAP
4. 3 ug+2 mM R-DOTAP
5. 0.6 ug+PBS
6. 0.6 ug+4 mM R-DOTAP
7. 0.6 ug+2 mM R-DOTAP The results are shown in FIG. 2. After the first injection (day 14 bleed), the cationic lipid-based vaccine demonstrated a superior increase in HAI titers. After injection 2 (day 35 bleed) the R-DOTAP based vaccine demonstrated a 2-8 fold increase in antibody induction potency depending on antigen and cationic lipids dose. After injection 2 (day 35 bleed), the low antigen dose vaccine with R-DOTAP is at least as potent as the high antigen dose commercial vaccine containing a 5-fold higher antigen dose.

EXAMPLE 4

Evaluation of the Protective Potency of a Cationic Lipid-Based Influenza Vaccine: Protective Hemagglutination Inhibition Assay Against Influenza Strain B Brisbane C57BL/6J mice were injected subcutaneously in the shaved flank with 100 µl to deliver a final dose of 3 µg or 0.6 µg of the antigen in either PBS, 4 mM R-DOTAP or 2 mM R-DOTAP. The mice were injected on day 0, then again with the identical formulation on day 21. Tail vein bleeds were performed on days 14 and 35.

Serum was stored frozen at −80° C. prior to testing. Samples were coded with respect to the treatment groups. A Hemagglutination inhibition assay was performed against the virus B Brisbane to quantify the antibody induction and protective efficacy of the vaccines.

Figure 3:
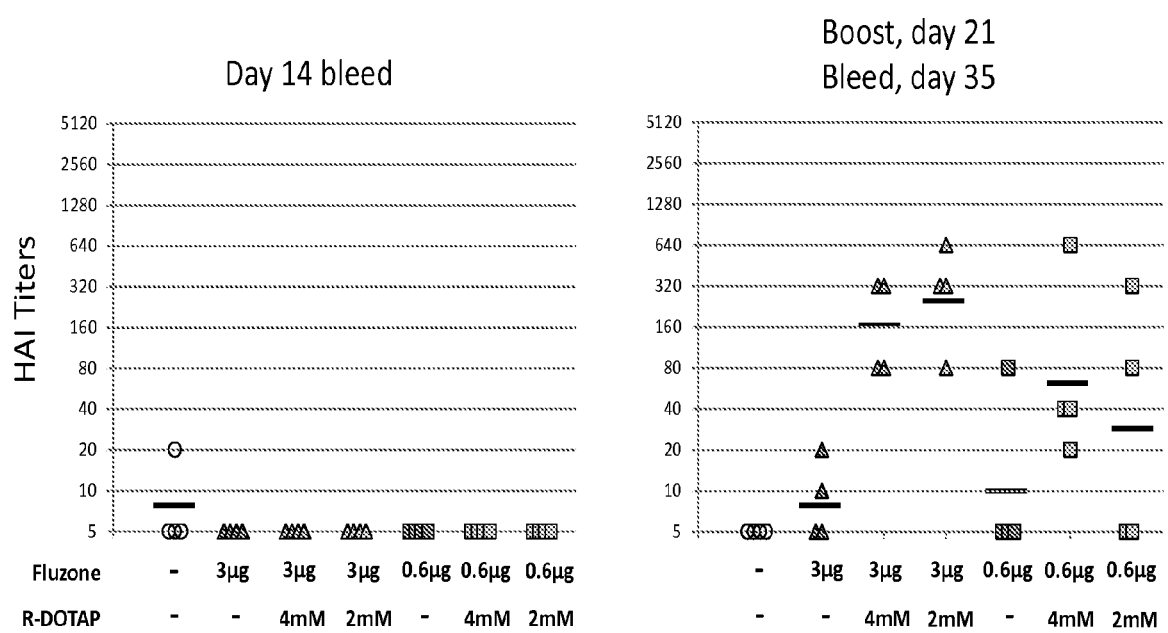
FIG. 3 shows results of a hemagglutination inhibition assay against B Brisbane with a commercial influenza vaccine and the cationic lipid-based influenza vaccines.

Four mice were tested per group:
1. Naïve
2. 3 ug+PBS
3. 3 ug+4 mM R-DOTAP
4. 3 ug+2 mM R-DOTAP
5. 0.6 ug+PBS
6. 0.6 ug+4 mM R-DOTAP
7. 0.6 ug+2 mM R-DOTAP The results are shown in FIG. 3. After the first injection (day 14 bleed), little difference between vaccines is observed with no vaccine providing significant titers. After injection 2 (day 35 bleed), the R-DOTAP based vaccine demonstrated a 4-35 fold increase in potency depending on antigen and cationic lipids dose. After injection 2 (day 35 bleed), the low antigen dose vaccine depending on R-DOTAP concentration is 4-8 times more potent than the high antigen dose commercial vaccine containing a 5-fold higher antigen dose.

EXAMPLE 5

Induction of CD8 T Cell Responses Following Vaccination with R-DOTAP H5N1 Influenza Vaccine There is considerable interest in developing an influenza vaccine to induce broadly cross-protective immunity to different subtypes of influenza. Existing TIV vaccines like Fluzone consist of mostly HA protein and do not generate significant CD8 T cell responses. Examples 2-4 show that R-DOTAP can greatly enhance the antibody response to HA after Fluzone vaccination.

There is a well-established CD8 T cell epitope within hemagglutinin from the mouse-adapted PR8 strain of virus (H1N1): $HA_{518-526}$, IYSTVASSL (SEQ ID NO:12), $K^d$ restricted. The peptide IYSTVASSL (SEQ ID NO:12) is used in an IFNγ ELISPOT assay, along with an irrelevant peptide to assess CD8 responses.

Approach:

Complete Freund's Adjuvant (CFA) was used as a positive control since CFA is known to offer cross-presentation of antigens will also stimulate CD8 T cell responses to whole ovalbumin. CFA cannot be used in vaccines due its induction of severe and potentially lethal inflammatory responses.

BALB/c Mice, 5 Mice/Group

Vaccinate on Day 0, boost on Day 7, perform ELISPOT on day 14.

A. Naive
B. CFA only
C. H5N1 vaccine, 3 ug/mouse

D. H5N1 vaccine, 3 ug/mouse+CFA
E. H5N1 vaccine, 3 ug/mouse+R-DOTAP 4 mM
F. R-DOTAP only (4 mM)

Day 14:

Sacrifice, remove spleens and perform ELISPOT with the $HA_{518-526}$ peptide and an unrelated peptide.

ELISPOT Assay

IFN-gamma ELISPOT plates; 2.5×105 splenocytes/well, stimulatory peptides: $HA_{518-526}$ and HPV $E_{629-38}$ (irrelevant peptide), both at 10 mM. The ELISPOT plates were developed and the plates scanned and IFN-gamma spots counted.

CONCLUSIONS

Figure 4:
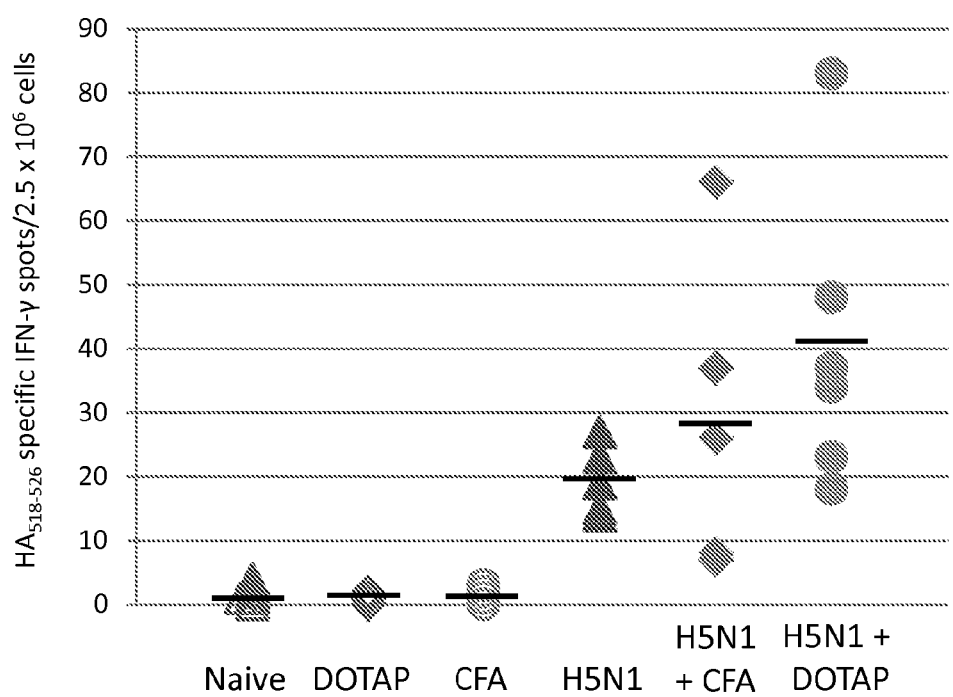
FIG. 4 shows that R-DOTAP enhances the T cell response to an internal class 1 restricted epitope of hemagglutinin. BALB/c mice were vaccinated with the H5N1 vaccine (inactivated A/Vietnam 2004) alone, or adjuvanted with either CFA (emulsion) or cationic lipid.

Specific ELISPOTS were obtained to the $HAS_{18-526}$ epitope after vaccination with H5N1 alone, and greater number of spots were obtained after adjuvanting with CFA or R-DOTAP (FIG. 4). CFA enhanced the H5N1 spots only modestly, whereas R-DOTAP stimulated a 2-fold enhancement of the response. The response was specific: very low numbers of spots in the no-peptide wells or in response to the irrelevant peptide. However, there were significant "background" spots in the wells from CFA vaccinated mice (up to 25 spots). This is in keeping with the high level of non-specific immune activation following CFA immunization.

Since vaccination was performed with the inactivated H5N1 vaccine containing full-length hemagglutinin and assayed for the T cell response to an internal, class 1-restricted peptide epitope, this is an indicator of "cross-presentation" involving the processing of an exogenous protein through the class I processing pathway. Therefore, R-DOTAP is demonstrated to significantly enhance cross presentation of an internal HA epitope that is known to be cross-protective in mouse experiments.

EXAMPLE 6

Evaluation of Antibody Responses to a Multi-Epitope Peptide Formulated with R-DOTAP HLA-A2 mice were injected subcutaneously with R-DOTAP formulated with HPV-16 E7 peptide (aa43-57). The mice were vaccinated on days 1, 21, and 42 and blood was drawn on day 57 and evaluated by ELISA for the induction of IgG and IgM antibodies to the peptide vaccine.

Results:

TABLE 1

Individual Antibody Immune Response Results ($E7_{43-57}$) - Log Titers

| Dose Group | Animal # | Pretest IgG | Day 57 IgG | Pretest IgM | Day 57 IgM |
|---|---|---|---|---|---|
| Group 1 | 104 | <2 | <2 | <2 | <2 |
| 0.086 mg | 110 | <2 | <2 | <2 | <2 |
| R-DOTAP | 854 | <2 | <2 | <2 | <2 |
| 0.00 mg | 941 | <2 | <2 | <2 | <2 |
| Peptide | 969 | <2 | <2 | <2 | <2 |
|  | 981 | <2 | <2 | <2 | 2 |
|  | 982 | <2 | <2 | <2 | <2 |
|  | 987 | <2 | <2 | <2 | 2 |
| Group 2 | 105 | <2 | <2 | <2 | <2 |
| 0.086 mg | 106 | <2 | <2 | <2 | <2 |
| R-DOTAP | 720 | n/a | <2 | n/a | <2 |
| 0.02 mg | 851 | <2 | <2 | <2 | 2 |
| Peptide | 984 | <2 | 2 | <2 | 2 |
|  | 988 | <2 | <2 | <2 | <2 |
|  | 992 | <2 | <2 | <2 | 2 |
|  | 996 | <2 | <2 | <2 | <2 |

CONCLUSIONS

When cationic lipid adjuvants are formulated with a T-cell epitope peptide antibody responses are negligible. However, strong CTL responses are observed.

EXAMPLE 7

Comparison of Immune Response in Cationic Lipid and Adjuvanted Vaccine Formulations The T-cell immune responses using vaccine formulations comprising varying cationic lipid nanoparticles and varying antigen assemblies were evaluated by ELISPOT. In this example, the vaccine formulations were be formulated using various cationic lipid nanoparticles DOEPC and DOTMA, and compared with the emulsion adjuvant Montanide™.

Various different vaccine formulations were evaluated in the present example. In one formulation, the antigen comprised the peptide antigen palmitoy-KSSGQAE-PDRAHYNIVTF [SEQ. ID. No. 3] (0.11 mM), and the cationic lipid DOEPC (1 mM). In a second formulation, the antigen comprised the peptide antigen palmitoy-KSSGQAEPDRAHYNIVTF [SEQ. ID. No. 3] (0.11 mM), and the cationic lipid DOTMA (1 mM). In a third formulation, the antigen assembly comprised the modified peptide antigen [SEQ. ID. No. 3] (0.11 mM) and the emulsion adjuvant Montanide™.

T-cell potency of the various vaccine formulations was evaluated by determining the antigen-specific immune response via ELISPOT to the T-cell epitope peptide HPV-16 $E7_{49-57}$ RAHYNIVTF [SEQ. ID. No. 2].

CONCLUSIONS

Figure 5:
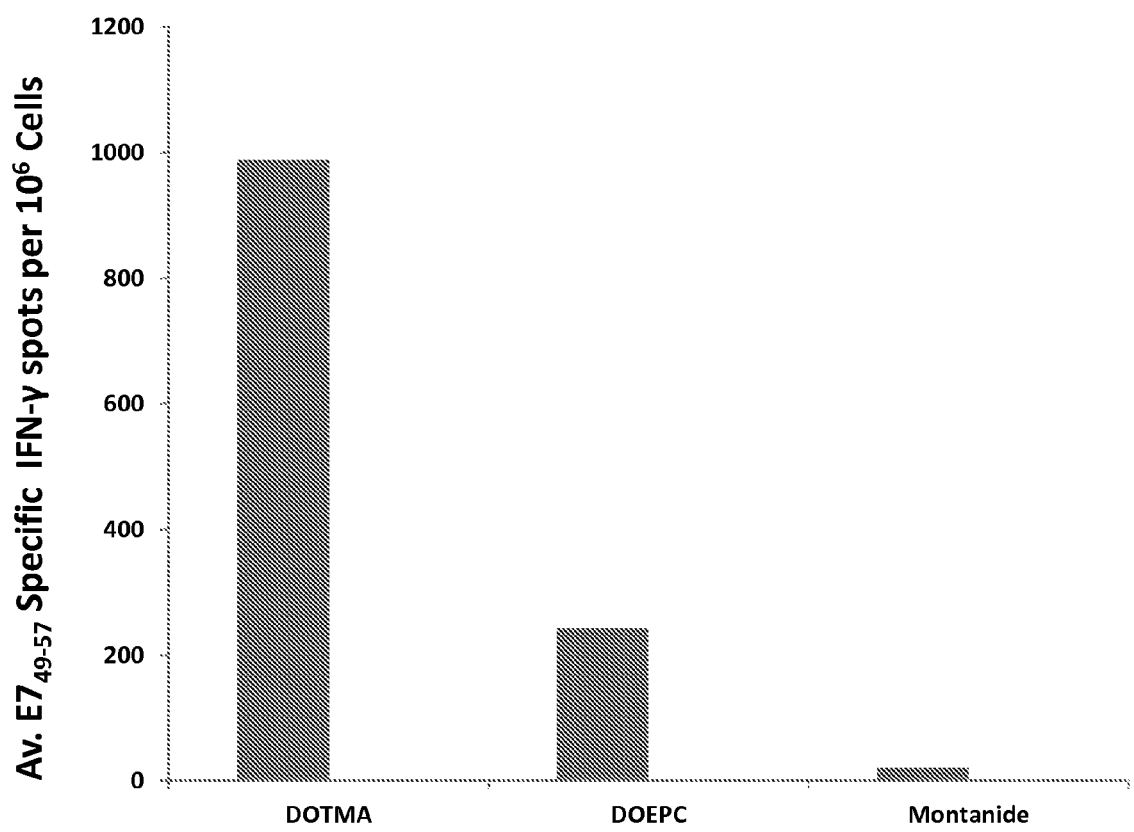
FIG. 5 shows that DOTMA and DOEPC enhance the T cell response to a class I restricted epitope of the human papillomavirus Strain 16. C5713L/6 mice were vaccinated with the various formulations consisting of the cationic lipid adjuvants or Montanide™ and the peptide HPV-16 E743-57. Superior T-cell enhancement results with the use of the cationic lipids compared to Montanide™.

Specific ELISPOTS were obtained to the $E7_{49-57}$ epitope after vaccination of DOTMA, DOEPC and Montanide™, each formulated with SEQ1. A greater number of spots was obtained after formulating with the cationic lipids DOTMA or DOEPC compared to the Montanide™ adjuvant (see FIG. 5). This example demonstrates show that the cationic lipids act as potent immunomodulatory adjuvants and induce superior CD8+ T-cell immune responses compared to the emulsion adjuvant Montanide™.

EXAMPLE 8

Induction of CD8 T Cell Responses Following Vaccination with DOTMA or DOEPC H5N1 Influenza Vaccine There is a well-established CD8 T cell epitope within hemagglutinin from the mouse-adapted PR8 strain of virus (H1N1): $HA_{518-526}$, IYSTVASSL (SEQ ID NO:12), $K^d$ restricted. The peptide IYSTVASSL (SEQ ID NO:12) is used in an IFNγ ELISPOT assay, along with an irrelevant peptide to assess CD8 responses. In the present example, DOTMA or DOEPC (including enantiomers of each) may be used as the exemplary cationic lipids.

Approach:

Complete Freund's Adjuvant (CFA) can be used as a positive control since CFA is known to offer cross-presentation of antigens will also stimulate CD8 T cell responses to whole ovalbumin. CFA cannot be used in vaccines due its induction of severe and potentially lethal inflammatory responses.

BALB/c Mice, 5 Mice/Group can be Evaluated
Vaccinate on Day 0, boost on Day 7, perform ELISPOT on day 14.
  A. Naive
  B. CFA only
  C. H5N1 vaccine, 3 ug/mouse
  D. H5N1 vaccine, 3 ug/mouse+CFA
  E. H5N1 vaccine, 3 ug/mouse+R-DOTAP 4 mM
  F. R-DOTAP only (4 mM)

Day 14:

Sacrifice, remove spleens and perform ELISPOT with the HA$_{518-526}$ peptide and an unrelated peptide.

ELISPOT Assay

IFN-gamma ELISPOT plates; 2.5×105 splenocytes/well, stimulatory peptides: HA$_{518-526}$ and HPV E$_{629-38}$ (irrelevant peptide), both at 10 mM. The ELISPOT plates can be developed and the plates can be scanned and IFN-gamma spots can be counted.

The invention claimed is:

1. A lipid-based vaccine composition comprising a lipid and at least one pathogenic antigen,
   wherein the lipid consists of a cationic lipid and wherein the cationic lipid consists of R-DOTAP;
   wherein the at least one pathogenic antigen is a multi-epitope influenza antigen,
   wherein the vaccine composition is capable of enhancing both a CD 8+ T cell response and an antibody response over the at least one pathogenic antigen alone, and
   wherein the CD 8+ T-cell response is enhanced by at least 2 fold over that elicited by the antigen alone.

2. The vaccine composition of claim 1, wherein the at least one pathogenic antigen is a naturally-occurring, an inactivated, synthetic or a recombinant antigen.

3. The vaccine composition of claim 2, wherein the inactivated pathogenic antigen comprises an antigen from a conserved region of a pathogen.

4. The vaccine composition of claim 3, wherein the inactivated pathogenic antigen consists of hemagglutinin antigen(s).

5. The vaccine composition of claim 1, wherein the multi-epitope influenza antigen comprises a recombinant influenza antigen.

6. A method of effecting antigen cross presentation to induce a humoral immune response and a cellular immune response in a mammal, said method comprising the step of administering an effective amount of a vaccine composition to the mammal, wherein the vaccine composition comprises a lipid, and at least one pathogenic antigen,
   wherein the lipid consists of a cationic lipid and wherein the cationic lipid consists of R-DOTAP.

7. The method of claim 6 wherein the humoral immune response is an antibody response.

8. The method of claim 6 wherein the cellular immune response is a T cell response.

9. The method of claim 8 wherein the T cell response is a CD 8+ T cell response.

10. The method of claim 6 wherein the cationic lipid is a non-steroidal cationic lipid.

11. The vaccine composition of claim 5, wherein the inactivated pathogenic antigen consists of a neuraminidase subunit vaccine.

12. The vaccine composition of claim 2, where the inactivated pathogenic antigen is a recombinant protein.

13. The vaccine composition of claim 2, wherein the inactivated pathogenic antigen is a lipidated antigen or an antigen modified to increase hydrophobicity of the antigen.

14. The vaccine composition of claim 2, wherein the inactivated pathogenic antigen encodes a modified protein or peptide.

15. The vaccine composition of claim 14, wherein the modified protein or peptide is bonded to a hydrophobic group.

16. The vaccine composition of claim 15, wherein the modified protein or peptide bonded to a hydrophobic group further comprises a linker sequence between the antigen and the hydrophobic group.

17. The vaccine composition of claim 15, wherein the hydrophobic group is a palmitoyl group.

18. The vaccine composition of claim 1, further comprising a non-ionic buffer, and wherein the vaccine composition is free of phosphate buffered saline (PBS).

* * * * *

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Arg Ala His Tyr Asn Ile Val Thr Phe
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Gln Ala Glu Pro Asp Arg Ala His Tyr Asn Ile Val Thr Phe
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Lys Ser Ser Gly Gln Ala Glu Pro Asp Arg Ala His Tyr Asn Ile Val
1               5                   10                  15

Thr Phe

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Tyr Met Leu Asp Leu Gln Pro Glu Thr Thr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Lys Ser Ser Tyr Met Leu Asp Leu Gln Pro Glu Thr Thr
```

```
<210> SEQ ID NO 6
<211> LENGTH: 23
<212> TYPE: PRT
<213> ORGANISM: Artificial Sequence
<220> FEATURE:
<223> OTHER INFORMATION: Synthetic

<400> SEQUENCE: 6

Lys Ser Ser Met His Gly Asp Thr Pro Thr Leu His Glu Tyr Met Leu
1               5                   10                  15

Asp Leu Gln Pro Glu Thr Thr
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic

<400> SEQUENCE: 7

Lys Ser Ser Leu Leu Met Gly Thr Leu Gly Ile Val Cys Pro Ile Cys
1               5                   10                  15

Ser Gln Lys Pro
            20

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Lys Val Pro Arg Asn Gln Asp Trp Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ser Tyr Val Asp Phe Phe Val Trp Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Lys Tyr Ile Cys Asn Ser Ser Cys Met
1               5

<210> SEQ ID NO 11
<211> LENGTH: 12
<212> TYPE: PRT
<213> ORGANISM: Artificial Sequence
<220> FEATURE:
```

```
<223> OTHER INFORMATION: Synthetic

<400> SEQUENCE: 11

Lys Ser Ser Lys Val Pro Arg Asn Gln Asp Trp Leu
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Ile Tyr Ser Thr Val Ala Ser Ser Leu
1               5
```